United States Patent
Miesse et al.

(10) Patent No.: US 9,655,758 B2
(45) Date of Patent: May 23, 2017

(54) DEVICES AND METHODS FACILITATING SLEEVE GASTRECTOMY PROCEDURES

(71) Applicant: Covidien LP, Mansfield, MA (US)

(72) Inventors: Andrew Miesse, Durham, CT (US);
Kurt Dierking, Louisville, KY (US);
Ben Morris, Jeffersonville, IN (US);
Greg Furnish, Louisville, KY (US);
John Miser, Crestwood, KY (US);
Alex Nadein, Louisville, KY (US);
Simon M. Furnish, Louisville, KY (US); Mark Griffin, Louisville, KY (US); Cory Celestino, Floyds Knobs, IN (US)

(73) Assignee: Covidien LP, Mansfield, MA (US)

( * ) Notice: Subject to any disclaimer, the term of this patent is extended or adjusted under 35 U.S.C. 154(b) by 132 days.

(21) Appl. No.: 14/492,712

(22) Filed: Sep. 22, 2014

(65) Prior Publication Data
US 2015/0133772 A1    May 14, 2015

Related U.S. Application Data

(60) Provisional application No. 61/902,463, filed on Nov. 11, 2013.

(51) Int. Cl.
*A61F 5/00* (2006.01)
*A61B 1/273* (2006.01)
(Continued)

(52) U.S. Cl.
CPC ............ *A61F 5/0089* (2013.01); *A61B 5/065* (2013.01); *A61B 17/0218* (2013.01);
(Continued)

(58) Field of Classification Search
CPC ...... A61F 5/0003; A61F 5/0013; A61F 5/003; A61F 5/0036; A61F 5/004; A61F 5/0069;
(Continued)

(56) References Cited

U.S. PATENT DOCUMENTS

| 2,067,031 A | 1/1937 | Wappler |
| 3,739,784 A | 6/1973 | Itoh |

(Continued)

FOREIGN PATENT DOCUMENTS

| CN | 201365906 Y | 12/2009 |
| CN | 102626536 A | 8/2012 |

(Continued)

OTHER PUBLICATIONS

European Search Report, dated Mar. 19, 2015, corresponding to European Application No. 14192226.0; 7 pages.

(Continued)

*Primary Examiner* — Todd J Scherbel

(57) ABSTRACT

A gastrectomy device includes an elongated member defining a centerline that extends through proximal and distal ends thereof. A shape modification member coupled to the elongated member is movable relative to the centerline of the elongated member. The shape modification member is movable between a first state, adjacent to the elongated member, and a second state, spaced from the elongated member. The shape modification member conforms to a portion of a patient's stomach in the second state.

19 Claims, 27 Drawing Sheets

(51) Int. Cl.
  *A61B 5/06* (2006.01)
  *A61B 17/02* (2006.01)
  *A61B 17/072* (2006.01)
  *A61B 17/22* (2006.01)
  *A61B 17/29* (2006.01)
  *A61M 25/10* (2013.01)
  *A61B 17/00* (2006.01)
  *A61B 17/30* (2006.01)
  *A61B 90/00* (2016.01)
  *A61B 90/30* (2016.01)

(52) U.S. Cl.
  CPC ........ *A61B 17/07207* (2013.01); *A61B 17/22* (2013.01); *A61B 17/29* (2013.01); *A61F 5/0083* (2013.01); *A61M 25/10* (2013.01); *A61B 2017/00278* (2013.01); *A61B 2017/00314* (2013.01); *A61B 2017/00323* (2013.01); *A61B 2017/00566* (2013.01); *A61B 2017/00818* (2013.01); *A61B 2017/00876* (2013.01); *A61B 2017/00986* (2013.01); *A61B 2017/07214* (2013.01); *A61B 2017/22052* (2013.01); *A61B 2017/22055* (2013.01); *A61B 2017/22069* (2013.01); *A61B 2017/306* (2013.01); *A61B 2090/0807* (2016.02); *A61B 2090/309* (2016.02); *A61B 2090/3945* (2016.02); *A61B 2090/3958* (2016.02)

(58) Field of Classification Search
  CPC .... A61F 5/0076; A61F 5/0083; A61F 5/0086; A61F 5/0089; A61F 5/065; A61B 2017/00818; A61B 2090/0811; A61B 2090/3945
  See application file for complete search history.

(56) References Cited

U.S. PATENT DOCUMENTS

| | | | |
|---|---|---|---|
| 4,328,805 A | 5/1982 | Akopov et al. | |
| 4,403,604 A | 9/1983 | Wilkinson et al. | |
| 4,744,363 A | 5/1988 | Hasson | |
| 5,179,938 A | 1/1993 | Lonky | |
| 5,246,456 A | 9/1993 | Wilkinson | |
| 5,297,536 A | 3/1994 | Wilk | |
| 5,325,848 A | 7/1994 | Adams et al. | |
| 5,358,496 A | 10/1994 | Ortiz et al. | |
| 5,382,231 A | 1/1995 | Shlain | |
| 5,401,241 A | 3/1995 | Delany | |
| 5,458,131 A | 10/1995 | Wilk | |
| 5,465,709 A | 11/1995 | Dickie et al. | |
| 5,718,666 A | 2/1998 | Alarcon | |
| 7,153,131 B2 | 12/2006 | Crohn | |
| 8,092,378 B2 | 1/2012 | Roth et al. | |
| 8,147,502 B2 | 4/2012 | Albrecht et al. | |
| 8,192,448 B2 | 6/2012 | Bessler et al. | |
| 8,454,503 B2 | 6/2013 | Roth et al. | |
| 8,663,149 B2 | 3/2014 | Gagner et al. | |
| 2002/0091395 A1 | 7/2002 | Gabbay | |
| 2004/0006351 A1 | 1/2004 | Gannoe et al. | |
| 2004/0092974 A1 | 5/2004 | Gannoe et al. | |
| 2005/0119674 A1 | 6/2005 | Gingras | |
| 2005/0203489 A1 | 9/2005 | Saadat et al. | |
| 2005/0251158 A1 | 11/2005 | Saadat et al. | |
| 2006/0200004 A1 | 9/2006 | Wilk | |
| 2006/0241344 A1 | 10/2006 | Wilk | |
| 2006/0241570 A1 | 10/2006 | Wilk | |
| 2007/0032702 A1 | 2/2007 | Ortiz | |
| 2008/0249404 A1* | 10/2008 | Mikkaichi | A61B 17/00234 600/437 |
| 2009/0276055 A1 | 11/2009 | Harris et al. | |
| 2010/0179417 A1 | 7/2010 | Russo | |
| 2011/0178454 A1 | 7/2011 | Gagner et al. | |
| 2011/0288576 A1 | 11/2011 | Hoffman | |
| 2012/0165604 A1* | 6/2012 | Stokes | A61B 18/1492 600/104 |
| 2012/0165608 A1 | 6/2012 | Banik et al. | |
| 2012/0184981 A1 | 7/2012 | Pecor et al. | |
| 2012/0239061 A1 | 9/2012 | Mathur | |
| 2013/0165774 A1 | 6/2013 | Nocca | |
| 2014/0018722 A1 | 1/2014 | Scott et al. | |
| 2014/0114121 A1 | 4/2014 | Trivedi | |

FOREIGN PATENT DOCUMENTS

| | | |
|---|---|---|
| EP | 2246013 A1 | 11/2010 |
| ES | 2326937 A1 | 10/2009 |
| FR | 2708456 A1 | 2/1995 |
| JP | 3178309 U | 9/2012 |
| WO | 02096327 A2 | 12/2002 |
| WO | 03/075979 A2 | 9/2003 |
| WO | 2009097585 A1 | 8/2009 |
| WO | 2012138737 A1 | 10/2012 |
| WO | 2013123235 A1 | 8/2013 |
| WO | 2014062881 A1 | 4/2014 |

OTHER PUBLICATIONS

European Search Report, dated Mar. 24, 2015, corresponding to European Application No. 14192416.7; 7 pages.
Dietel et al., "Endoscopy of Vertical Banded Gastroplasty," The American Surgeon, May 1989, vol. 55; pp. 287-890.
Dietel et al., "Vertical Banded Gastroplasty: Results in 233 Patients," The Canadian Journal of Surgery, Sep. 1986, vol. 29, No. 5; pp. 322-324.
Mason et al., "Vertical Gastroplasty: Evolution of Vertical Banded Gastroplasty," World Journal of Surgery, Sep. 1998, vol. 22, No. 9; pp. 919-924.
Extended European Search Report dated Oct. 1, 2015, corresponding to European Application No. 15167342.3; 7 pages.
European Search Report dated Dec. 2, 2015, corresponding to European Application No. 15177233.2; 7 pages.
International Search Report and Written Opinion of hte International Searching Authoirity, dated Jul. 12, 2016, corresponding to International Application No. PCT/US2016/028046; 12 total pages.
Extended European Search Report dated Sep. 17, 2015, corresponding to European Patent Application 15167339.9; 10 pages.
European Search Report dated Oct. 4, 2016, corresponding to European Application No. 16178267.7; 7 pages.

* cited by examiner

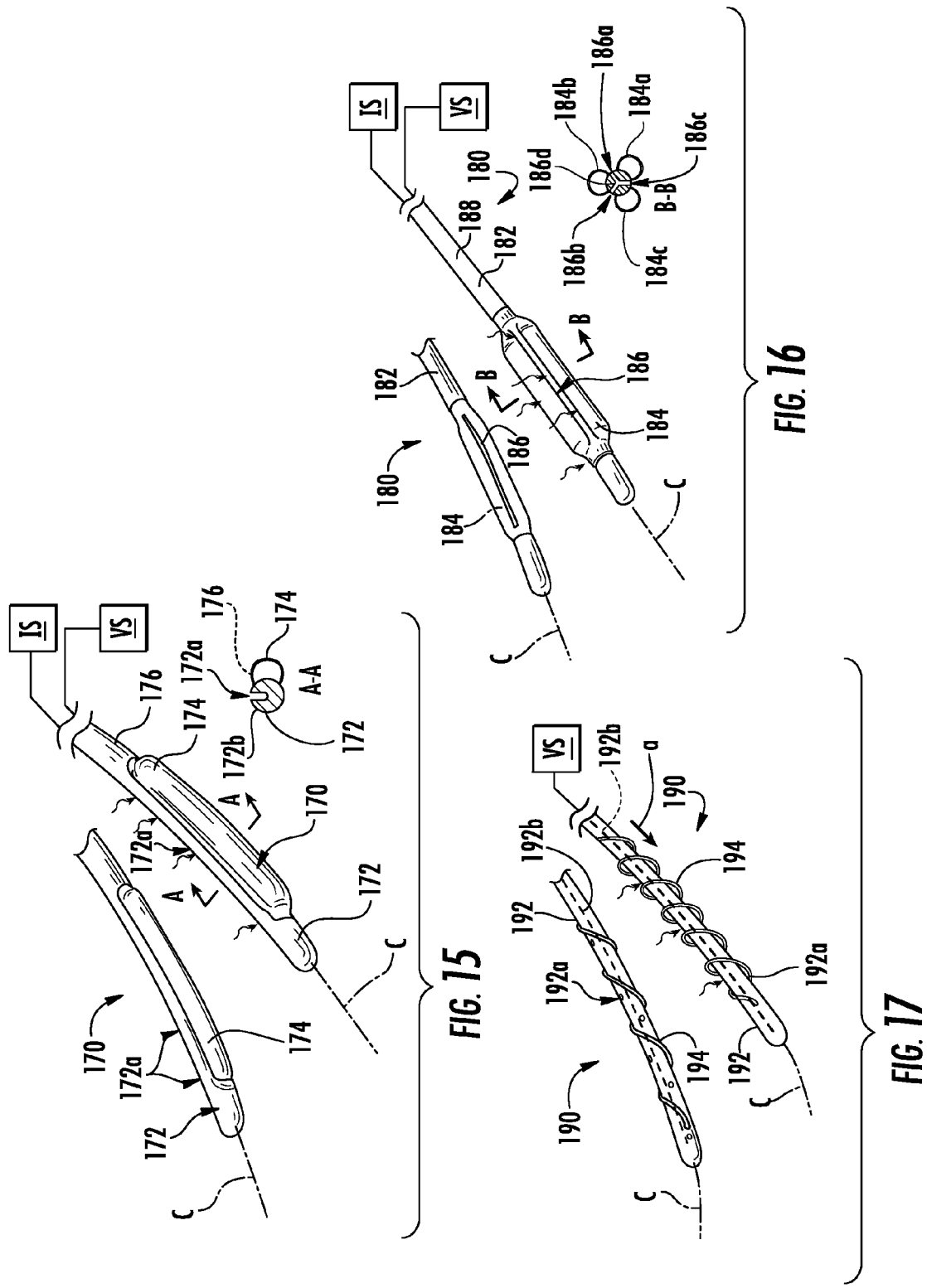

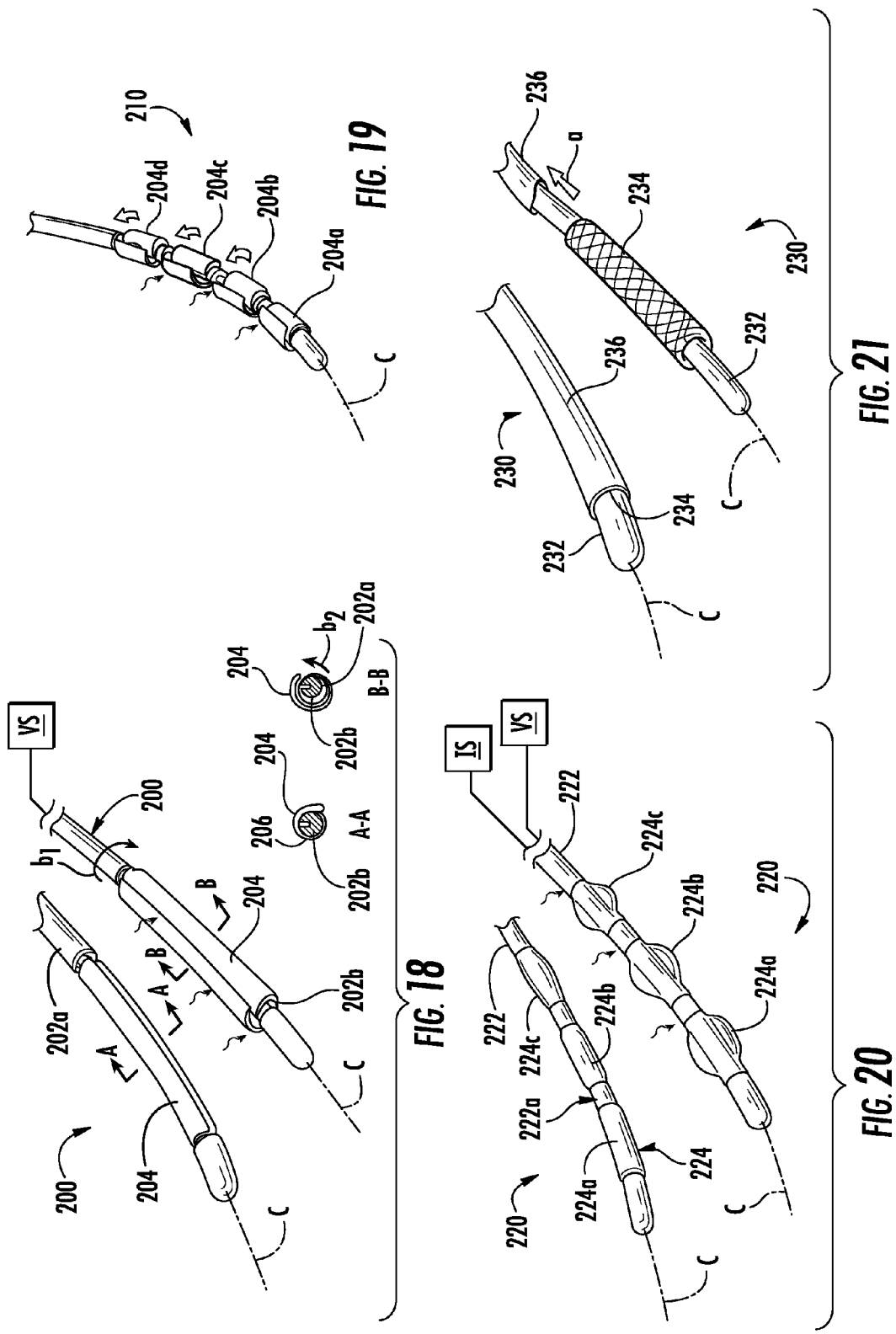

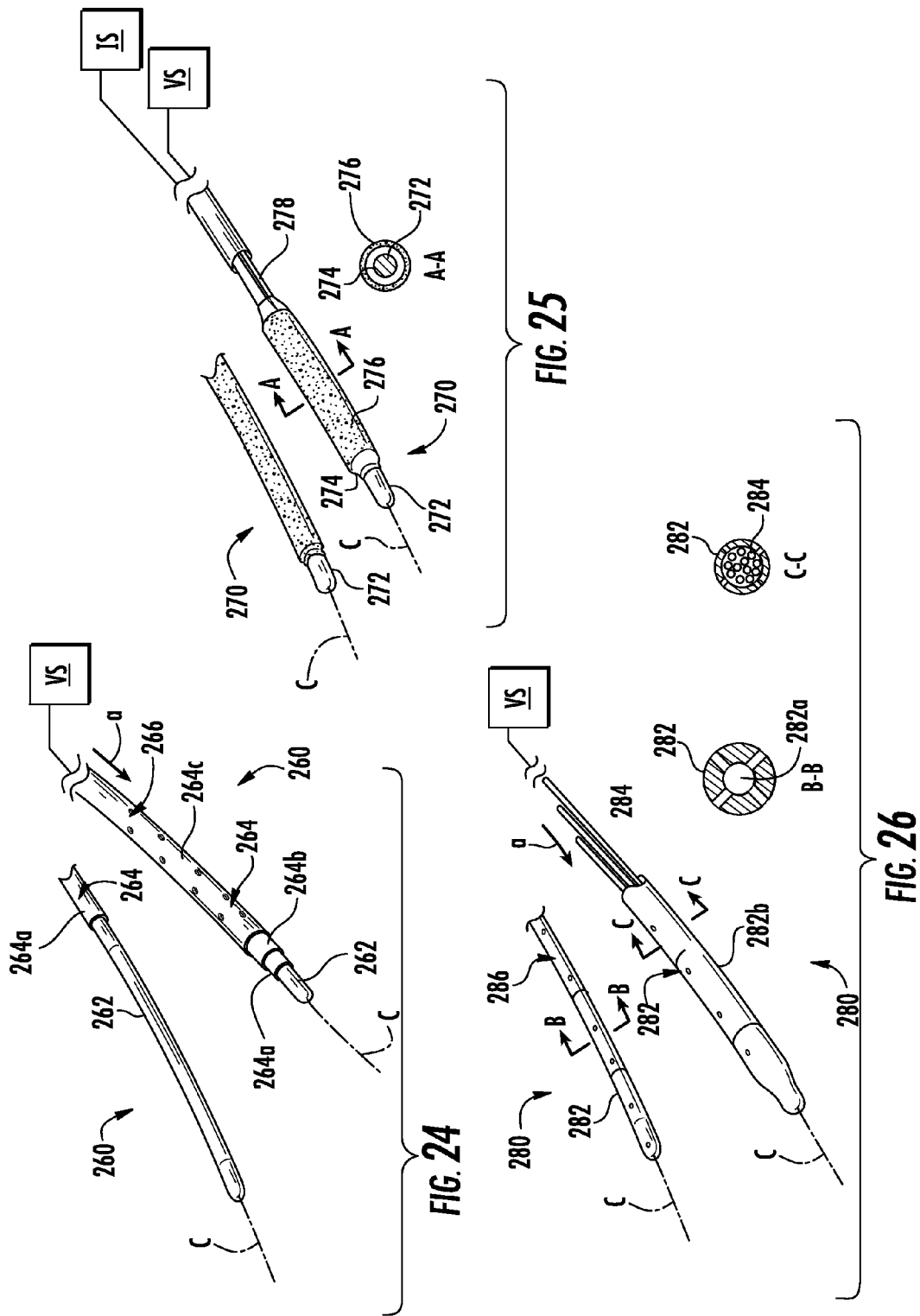

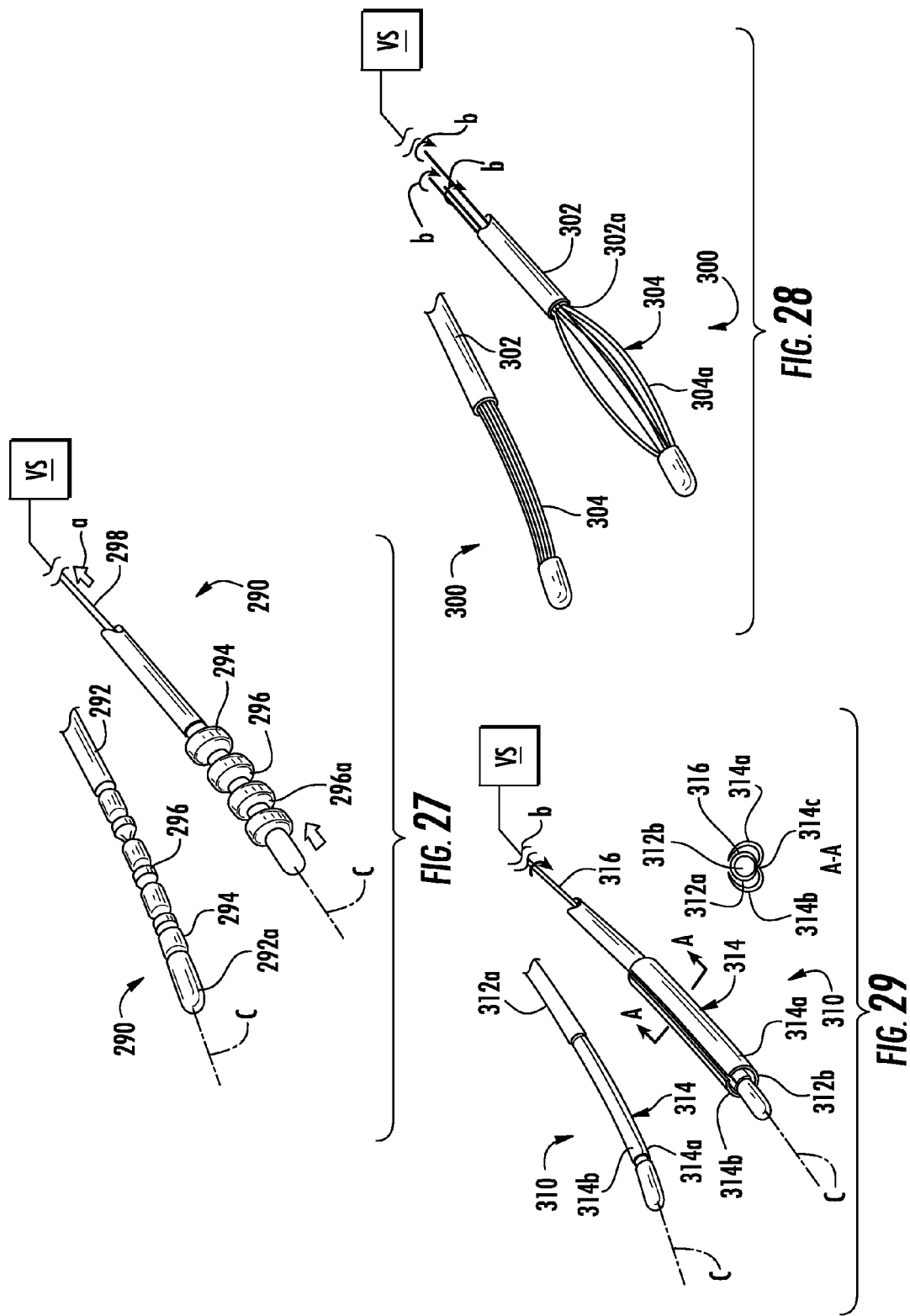

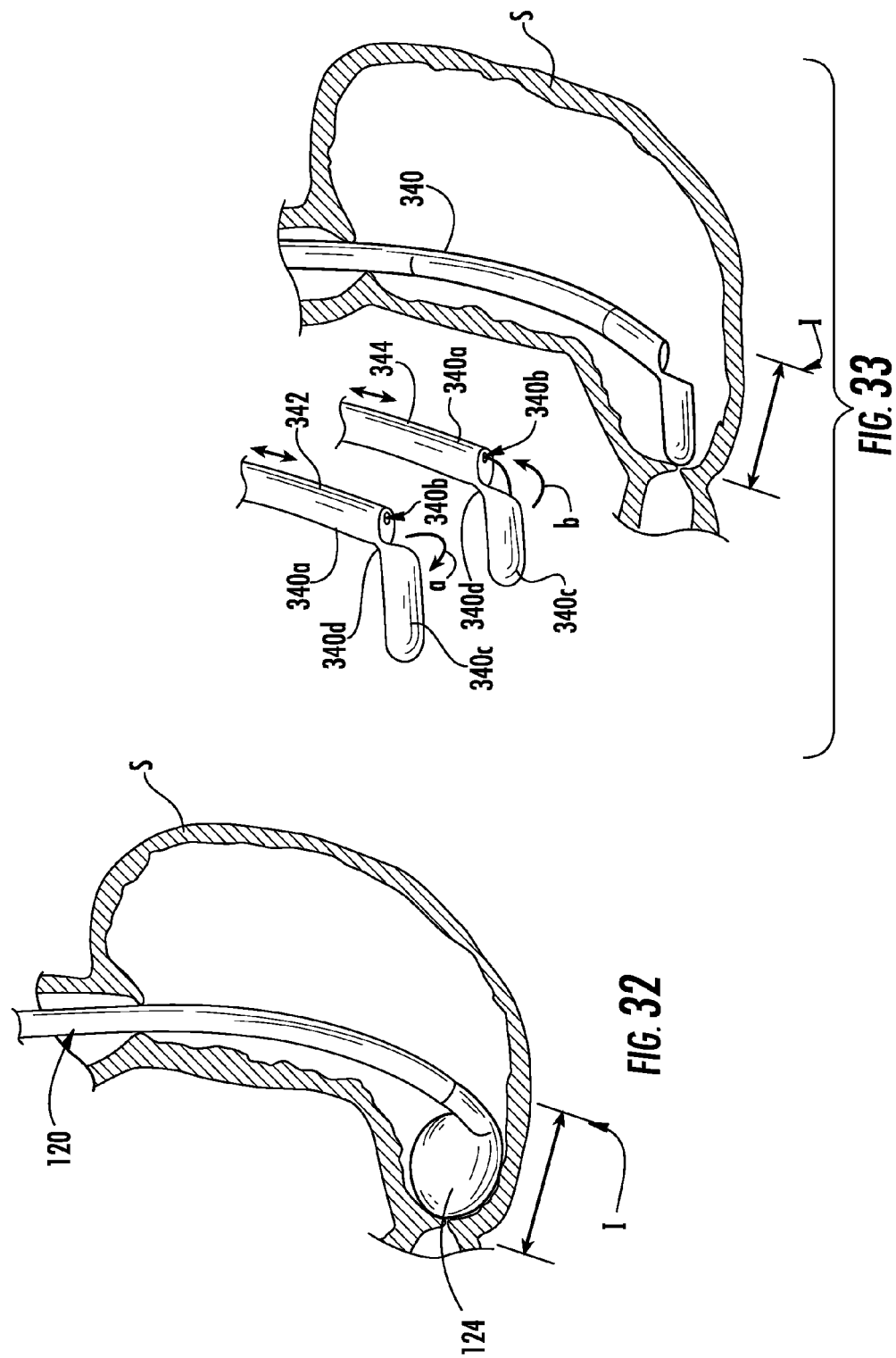

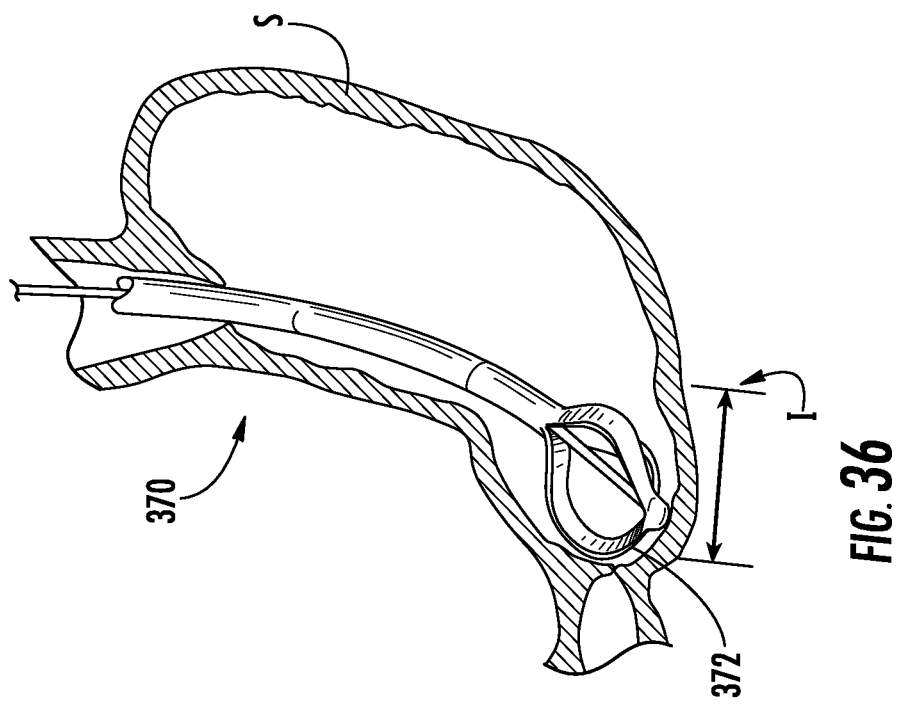
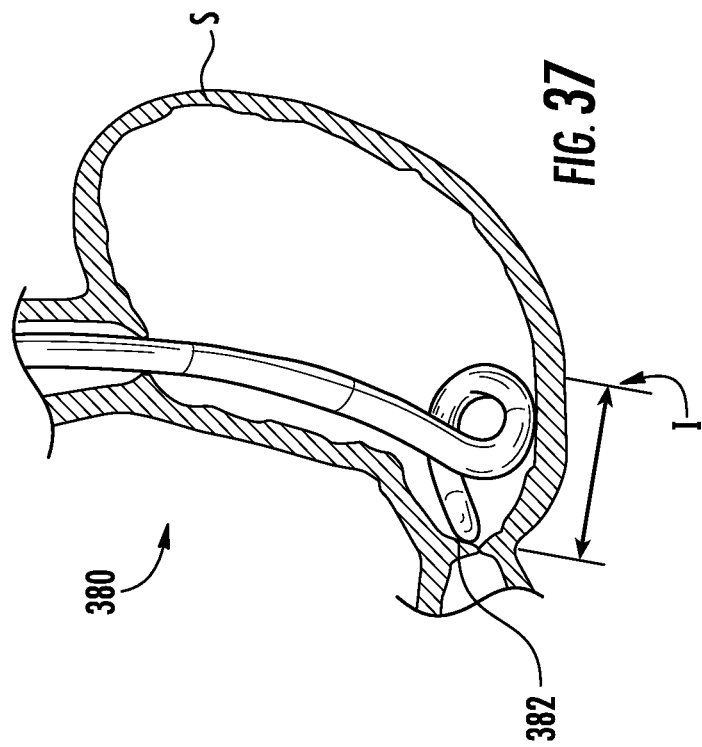

DEVICES AND METHODS FACILITATING SLEEVE GASTRECTOMY PROCEDURES

CROSS-REFERENCE TO RELATED APPLICATIONS

This application claims the benefit of U.S. Provisional Patent Application No. 61/902,463, filed Nov. 11, 2013, the entire disclosure of which is incorporated by reference herein.

TECHNICAL FIELD

The present disclosure relates generally to bariatric surgery and, more particularly, to devices and methods that facilitate performing sleeve gastrectomy procedures.

BACKGROUND

Obesity is reaching epidemic proportions in many regions of the world, particularly in the United States. In order to treat obesity, various surgical procedures have been developed including, for example, gastric bypass, adjustable gastric banding, and sleeve gastrectomy. The goal in each of these procedures is to reduce the patient's stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting the stomach, e.g., using a stapling device or other suitable device, to reduce the patient's stomach volume. Sleeve gastrectomy procedures are often aided by the use of a bougie, which serves as a guide or template for transecting the stomach to the appropriate configuration while inhibiting inadvertent transection of stomach or esophageal tissue. Once the stomach has been appropriately transected, the bougie is removed and a leak test is performed to determine whether there are any areas of extravasation.

SUMMARY

Gastrectomy devices for use in bariatric surgery are provided in accordance with the present disclosure.

In embodiments, a gastrectomy device includes an elongated flexible tube member, a balloon member, and a shape modification member.

In embodiments, a gastrectomy device includes a shaft having at least one expandable feature.

In some embodiments, a gastrectomy device includes at least one stapling location identifying feature.

In an aspect of the present disclosure, a gastrectomy device comprises: a tubular elongated member defining a centerline that extends through proximal and distal ends thereof, the elongate member defining a side opening; and a shape modification member being movable through the side opening of the elongated member and relative to the centerline of the elongated member between a first state, adjacent to the elongated member, and a second state, spaced from the elongated member, the shape modification member configured to conform to a portion of a patient's stomach in the second state, at least a portion of the shape modification member including one or more lights.

An expandable member coupled to the distal end of the elongated member can be included. The expandable member can be a balloon.

The elongated member is desirably formed of a flexible material. The elongated member can define a lumen that extends longitudinally therethrough, the elongated member defining at least one aperture in the distal end thereof that is in fluid communication with the lumen, the lumen configured to couple to a vacuum source. The shape modification member desirably forms an arc in the second state.

The shape modification member can be coupled to an actuator at a proximal end of the shape modification member, the actuator being movable to reposition the shape modification member between the first and second states. At least a portion of the shape modification member is desirably movable through the lumen and the side opening in response to linear movement of the shape modification member.

The elongated member can include a stress relief feature disposed at a predetermined distance from the distal end of the elongated member, the stress relief feature separating distal and proximal portions of the elongated member at a pivot point, the distal portion of the elongated member being pivotable relative to the proximal portion of the elongated member.

The shape modification member is desirably formed of a flexible material.

The shape modification member may be inflatable. The shape modification member can be configured to form at least one loop in the second state.

At least a portion of the shape modification member can be secured to a sleeve configured to slide along an outer surface of the elongated member to move the shape modification member between the first and second states.

A gastrectomy device includes: a tubular elongated member having an outer surface; and a shape modification member including a shaft that emerges from an opening in the elongated member, the shaft including a proximal portion and a distal portion, the distal portion of the shaft being movable between a first state adjacent the outer surface of the elongated member and a second state spaced from the outer surface of elongated member, the distal portion configured to conform to a greater curvature portion of a patient's stomach in the second state.

The device can have at least one expandable member coupled to the elongated member, the at least one expandable member being expandable relative to a centerline of the elongated member between a contracted state and an expanded state to facilitate selective securement of a distal end of the elongated member within a patient's stomach.

The elongated member can define a lumen that extends longitudinally therethrough, the elongated member defining at least one aperture in the distal end thereof that is in fluid communication with the lumen, the lumen configured to couple to a vacuum source.

In the gastrectomy device, at least a portion of the shape modification member may illuminate.

In another aspect, a method of performing a sleeve gastrectomy in the stomach comprises: inserting a tubular guide through the esophagus and into the stomach; extending an engaging member outwardly from the tubular guide against the greater curvature of the stomach; partially resecting the stomach using a surgical stapler; retracting the engaging member; and completing the resection of the stomach, forming a sleeve shaped portion of the stomach, and removing a remainder of the stomach.

The method can further comprise activating an array of lights.

In a further aspect, a method of performing a sleeve gastrectomy in the stomach comprises: inserting a tubular guide through the esophagus and into the stomach; extending an engaging member outwardly from the tubular guide against the greater curvature of the stomach; partially resecting the stomach using a surgical stapler; partially retracting the engaging member; partially resecting the stomach using the surgical stapler; retracting the engaging member; and completing the resection of the stomach, forming a sleeve shaped portion of the stomach, and removing a remainder of the stomach.

BRIEF DESCRIPTION OF THE DRAWINGS

Various aspects and features of the present disclosure are described herein with reference to the drawings wherein:

FIGS. 12-31 are views illustrating various embodiments of gastrectomy devices with a shafts having expandable features;

FIGS. 32-41 are views illustrating various embodiments of gastrectomy devices including stapling location identifying features;

DETAILED DESCRIPTION OF EMBODIMENTS

Figure 1:
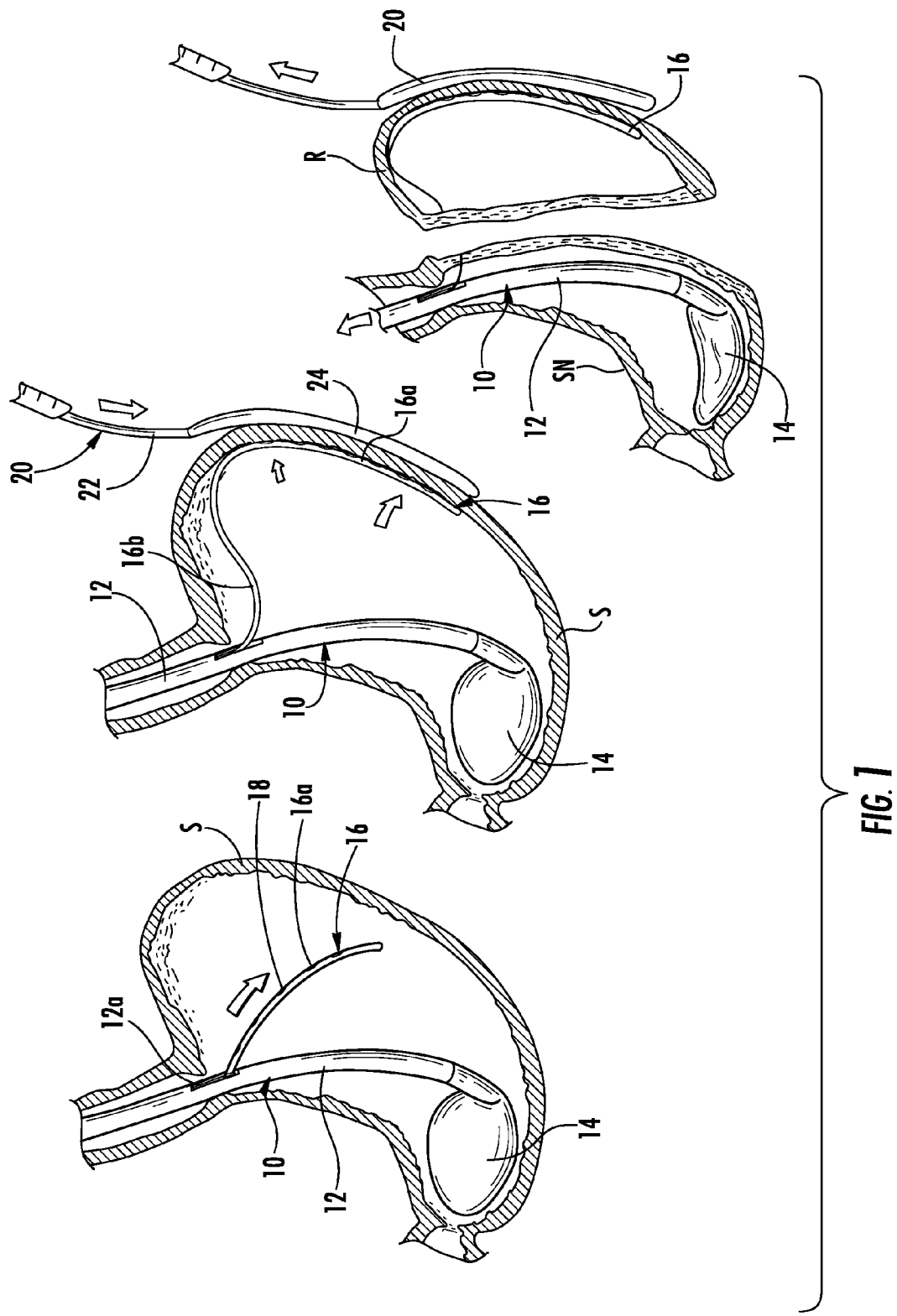
FIGS. 1-11 are progressive views of various embodiments of gastrectomy devices for effectuating gastrectomy procedures involving shape modification and/or remodeling.

Embodiments of the present disclosure are detailed below with reference to the drawings in which like reference numerals designate identical or corresponding elements in each of the several views. Throughout this description, the term "proximal" will refer to the portion of the device or component thereof that is closest to the user and the term "distal" will refer to the portion of the device or component thereof that is farthest from the user.

As depicted in FIGS. 1-11, embodiments of sleeve gastrectomy devices are provided in accordance with the present disclosure for effectuating gastrectomy procedures involving shape modification and/or remodeling.

Turning now to FIG. 1, one embodiment of a sleeve gastrectomy device is shown generally identified by reference numeral 10. Device 10 includes a tubular member 12 and an expandable balloon 14 supported on a distal end of tubular member 12. Tubular member 12 defines an aperture 12a through which a magnetic member 16 of device 10 can be advanced. Balloon 14 is selectively inflatable and deflatable, for example, in the antrum of the stomach "S" to position device 10 for effectuating a sleeve gastrectomy procedure. Magnetic member 16 includes a distal end portion 16a that supports one or more magnets 18 and/or magnetic material and a proximal end portion 16b. Magnetic member is advanced out of device 10 so that distal end portion 16a is positioned against an internal surface of stomach "S" for remodeling a curvature of stomach "S." A manipulation tool 20 having a shaft 22 that supports a capturing portion 24 can be positioned on an external surface of stomach "S" adjacent to distal end portion 16a of magnetic member 16 to magnetically secure distal end portion 16a to stomach "S." The stomach "S" can then be resected, as appropriate, separating the stomach "S" into a resected portion "R" and a new stomach portion "SN." One skilled in the art will realize that any number of open or laparoscopic stomach resection techniques/devices can be used including surgical staplers, vessel sealing devices, suturing and scalpels, etc. At some point prior to removal of device 10 and/or manipulation tool 20, the new stomach portion "SN" is tested for extravasation using any suitable technique, for example, by insufflating with saline and/or a dye, etc. The resected portion "R" can then be removed with distal end portion 16a, which is severed at proximal end portion 16b during resection, upon withdrawing manipulation tool 20 and balloon 14 can be deflated so that device 10 can be withdrawn.

Figure 2:
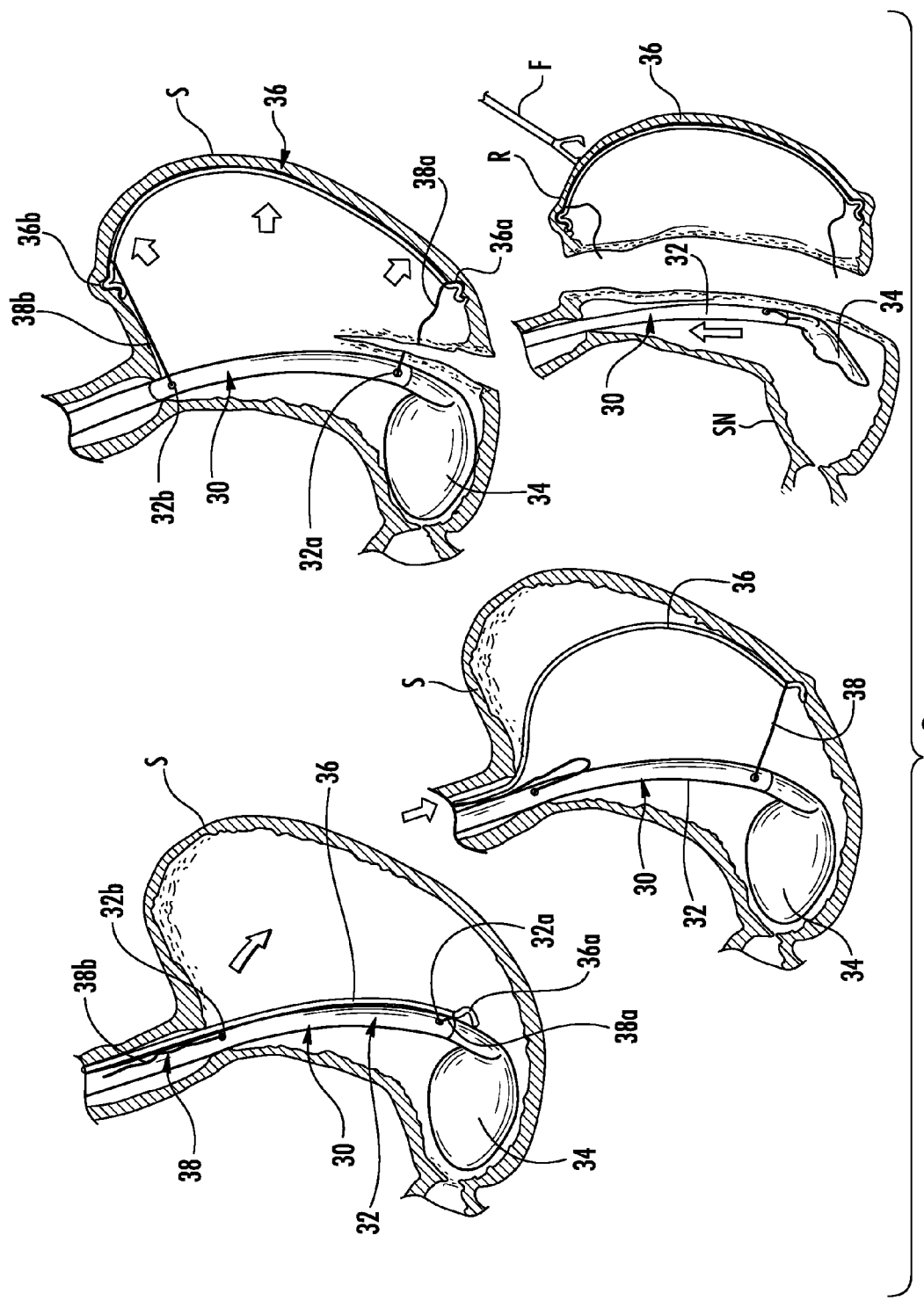

As seen in FIG. 2, another embodiment of a sleeve gastrectomy device is shown generally identified by reference numeral 30. Device 30 includes a tubular member 32 and an expandable balloon 34 supported on a distal end of tubular member 32. Tubular member 32 defines a first aperture 32a and a second aperture 32b. A form wire 36 is supported on tubular member 32 by suture 38. Form wire 36 includes a first wire anchor 36a on a distal end thereof and a second wire anchor 36b on a proximal end thereof. Suture 38 includes a first portion 38a and a second portion 38b, each of which may be separate sutures. To support form wire 36 on tubular member 32, first portion 38a extends through first aperture 32a and is secured to a distal end portion of form wire 36 and second portion 38b extends through second aperture 32b and is secured to a proximal end portion form wire 36.

Similar to balloon 14, balloon 34 is selectively inflated in the antrum of stomach "S" to position device 30 for effectuating a sleeve gastrectomy procedure. Suture 38 is advanced out of device 30 so that form wire 36 separates from tubular member 32 and spring biases against an internal surface of stomach "S" so that wire anchors 36a and 36b secure form wire 36 to stomach "S" for remodeling a curvature of stomach "S." The stomach "S" can then be resected, as appropriate, separating the stomach "S" into a resected portion "R" and a new stomach portion "SN." The new stomach portion "SN" can be tested for extravasation as described above. The resected portion "R" can be grasped by a separate forceps "F" and removed with form wire 36, which is separated from tubular member 32 when the suture 38 is severed during resection, and balloon 34 can be deflated so that device 30 can be withdrawn.

Figure 3:
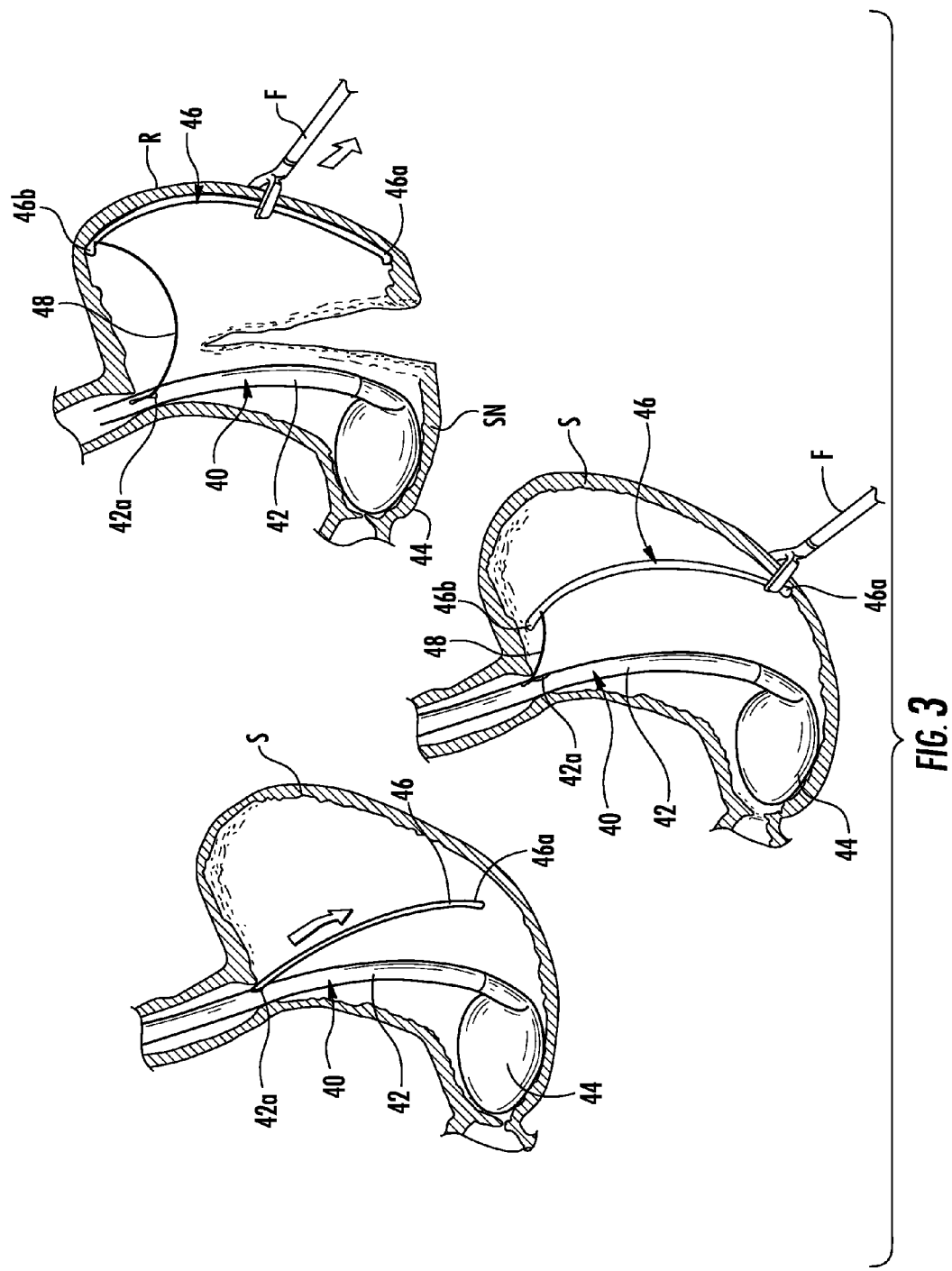

Turning now to FIG. 3, yet another embodiment of a sleeve gastrectomy device is shown generally identified by reference numeral 40. Device 40 includes a tubular member 42 and an expandable balloon 44 supported on a distal end of tubular member 42. Tubular member 42 defines an aperture 42a. A rigid forming member 46 is advanceable through tubular member 42 and out of aperture 42a and has a suture 48 secured to a proximal end portion thereof. Rigid forming member 46 includes a first anchor 46a on a distal end thereof and a second anchor 46b on a proximal end thereof.

Similar to balloon 14, balloon 44 is selectively inflated in the antrum of stomach "S" to position device 40 for effectuating a sleeve gastrectomy procedure. Rigid forming member 46 is advanced out of device 40 until suture 48 extends through aperture 42a so that first anchor 46a of rigid forming member 46 can be positioned against an internal surface of stomach "S." A separate forceps "F" can then grasp rigid forming member 46 from an external surface of stomach "S" to support rigid forming member 46 against stomach "S." Then, rigid forming member 46 can be positioned flush against the internal surface of stomach "S" so that anchors 46a, 46b and forceps "F," which is positioned centrally on rigid forming member 46, secure rigid forming member 46 to stomach "S" for remodeling a curvature of stomach "S." Stomach "S" can then be resected, as appropriate, separating the stomach "S" into a resected portion "R" and a new stomach portion "SN." The new stomach portion "SN" can be tested for extravasation as described above. The resected portion "R" and rigid forming member 46, which is separated from tubular member 42 when suture 48 is severed during resection, can be removed by forceps "F," and balloon 44 can be deflated so that device 40 can be withdrawn.

Figure 4:
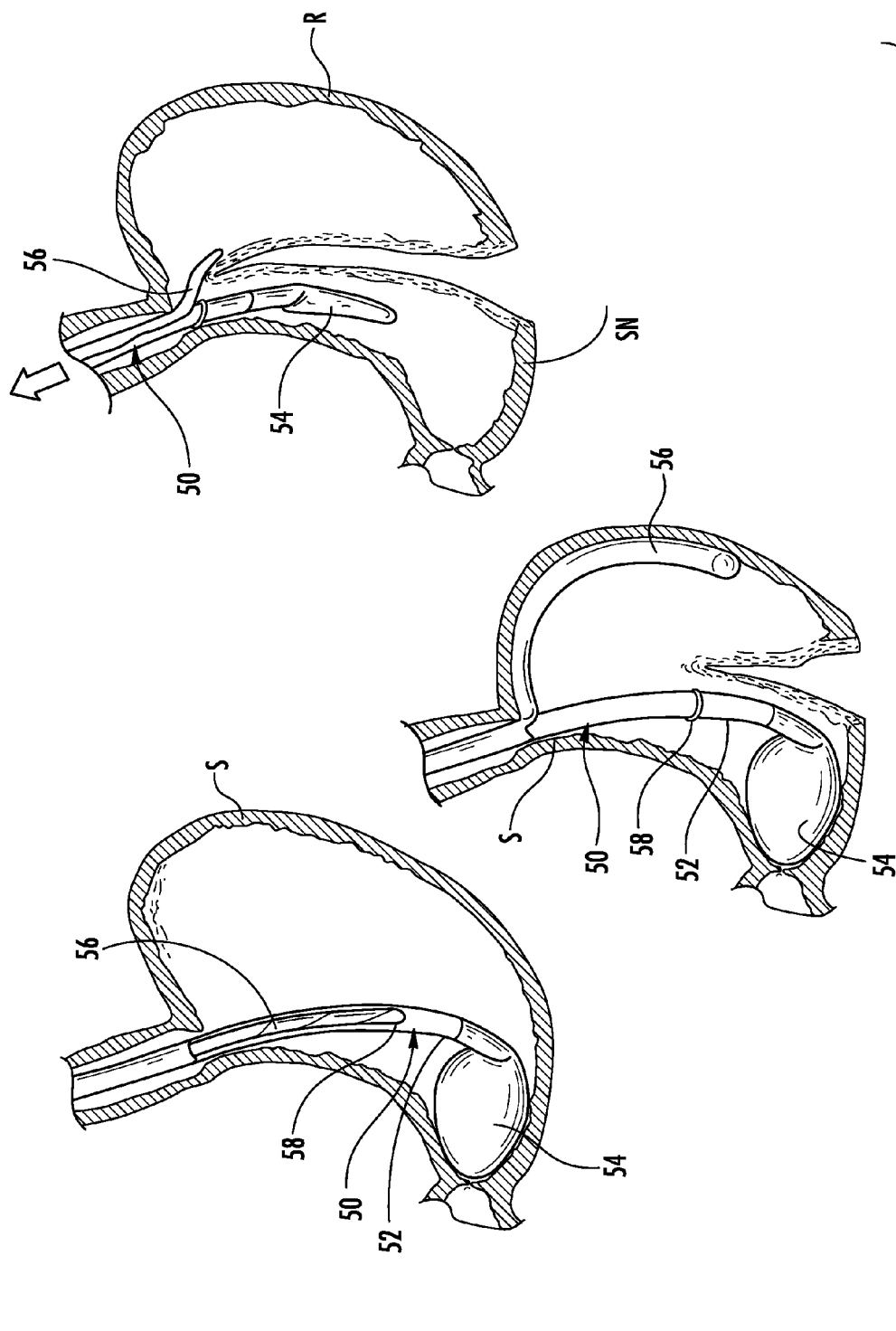

As seen in FIG. 4, one embodiment of a sleeve gastrectomy device is shown generally identified by reference numeral 50. Device 50 includes a tubular member 52 and a first expandable balloon 54 supported on a distal end of tubular member 52 and a second expandable balloon 56 supported on tubular member 52 proximally of first expandable balloon 54. The second balloon 56 can have a non-compliant shape. A distal end portion of second balloon 56 can be temporarily secured to tubular member 52 via suture 58.

Similar to balloon 14, balloon 54 is selectively inflated in the antrum of stomach "S" to position device 50 for effectuating a sleeve gastrectomy procedure. Second balloon 56 is inflated against an internal surface of stomach "S" for remodeling a curvature of stomach "S." The stomach "S" can then be at least partially resected, as appropriate, separating the stomach "S" into a resected portion "R" and a new stomach portion "SN." Before completion of the resection, first and second balloons 54, 56 can be deflated and device 50 can be withdrawn so that resection can be completed. Upon completion of the resection, the new stomach portion "SN" can be tested for extravasation as described above. The resected portion "R" can be grasped by a separate forceps "F" and removed.

Figure 5:
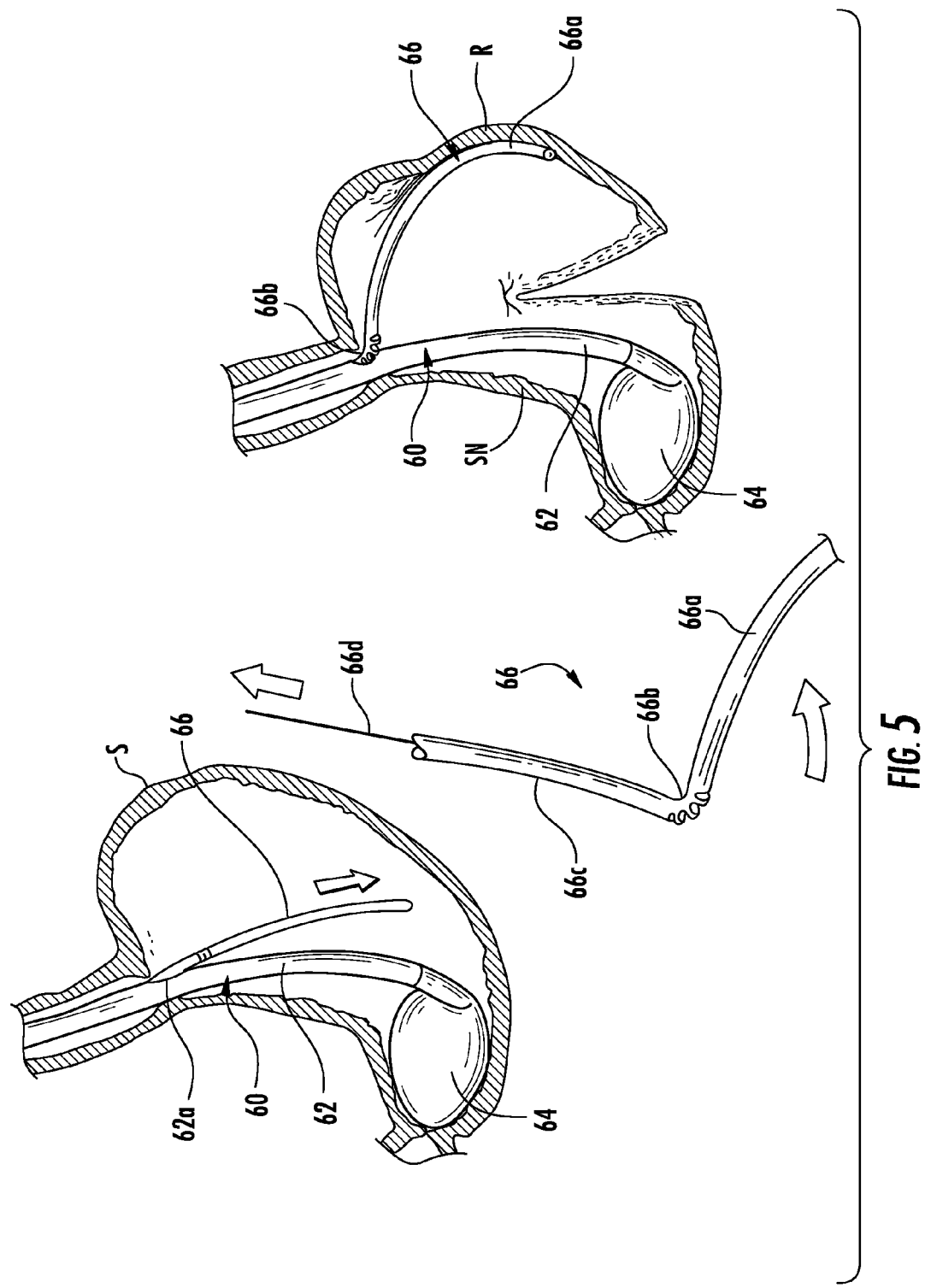

Turning now to FIG. 5, still another embodiment of a sleeve gastrectomy device is shown generally identified by reference numeral 60. Device 60 includes a tubular member 62 and an expandable balloon 64 supported on a distal end of tubular member 62. Tubular member 62 defines an aperture 62a, out of which, an articulating member 66 can be advanced. Articulating member 66 includes a distal end portion 66a, a pivot portion 66b, a proximal end portion 66c, and an articulation pull wire 66d that is secured to distal end portion 66a.

Similar to balloon 14, balloon 64 is selectively inflated in the antrum of stomach "S" to position device 60 for effectuating a sleeve gastrectomy procedure. Distal end portion 66a is advanced out of device 60 so that a proximally pulling of pull wire 66d pivots distal end portion 66a relative to proximal end portion 66c about pivot portion 66b to position distal end portion 66a against an internal surface of stomach "S" for remodeling a curvature of stomach "S." The stomach "S" can then be at least partially resected, as appropriate, separating the stomach "S" into a resected portion "R" and a new stomach portion "SN." Before completion of the resection, articulation member 66 can be withdrawn so that resection can be completed. Upon completion of the resection, the new stomach portion "SN" can be tested for extravasation as described above. The resected portion "R" can be grasped by a separate forceps "F" and removed, and balloon 64 can be deflated so that device 60 can be withdrawn.

Figure 6:
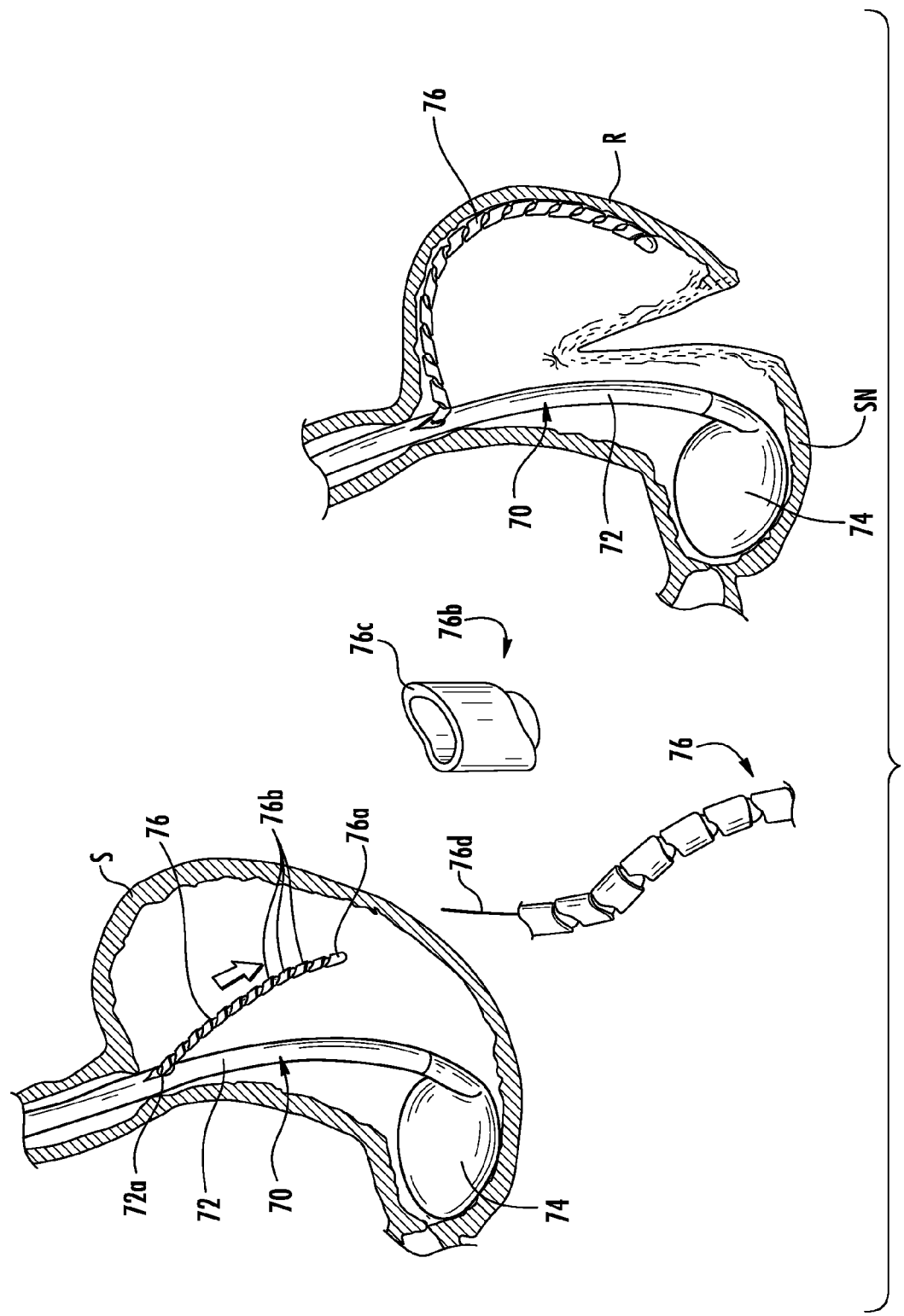

Turning now to FIG. 6, still another embodiment of a sleeve gastrectomy device is shown generally identified by reference numeral 70. Device 70 includes a tubular member 72 and an expandable balloon 74 supported on a distal end of tubular member 72. Tubular member 72 defines an aperture 72a, out of which, an articulating spine 76 can be advanced. Articulating spine 76 includes a distal end portion 76a and a plurality of vertebral members 76b. Each vertebral member of the plurality of vertebral members 76b defines a pull wire lumen 76c dimensioned to receive a pull wire 76d therethrough. The pull wire 76d is secured to distal end portion 76a, extends through each pull wire lumen 76c, and couples the plurality of vertebral members 76b together with distal end portion 76a.

Similar to balloon 14, balloon 74 is selectively inflated in the antrum of stomach "S" to position device 70 for effectuating a sleeve gastrectomy procedure. Distal end portion 76a and at least some of the plurality of vertebral members 76b are advanced out of device 70 so that a proximal pulling of pull wire 76d articulates articulating spine 76 to that at least some of the plurality of vertebral members 76b abut against an internal surface of stomach "S" for remodeling a curvature of stomach "S," which can be a predetermined curvature. The stomach "S" can then be at least partially resected, as appropriate, separating the stomach "S" into a resected portion "R" and a new stomach portion "SN." Before completion of the resection, articulation spine 76 can be withdrawn so that resection can be completed. Upon completion of the resection, the new stomach portion "SN" can be tested for extravasation as described above. The resected portion "R" can be grasped by a separate forceps and removed, and balloon 74 can be deflated so that device 70 can be withdrawn.

Figure 7:
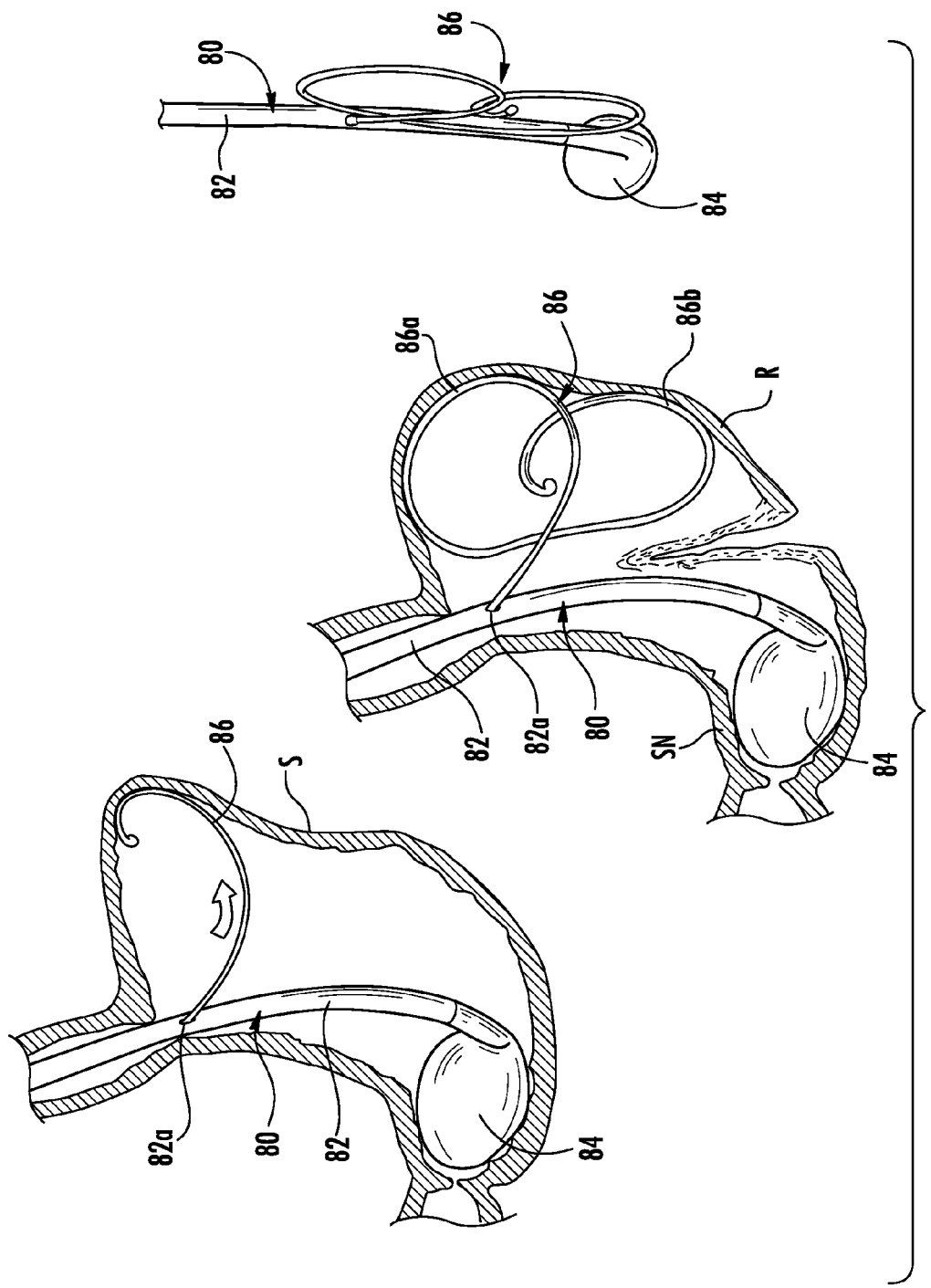

As seen in FIG. 7, yet another embodiment of a sleeve gastrectomy device is shown generally identified by reference numeral 80. Device 80 includes a tubular member 82 and an expandable balloon 84 supported on a distal end of tubular member 82. Tubular member 82 defines an aperture 82a, out of which, a flexible wire form 86 can be advanced.

Similar to balloon 14, balloon 84 is selectively inflated in the antrum of stomach "S" to position device 80 for effectuating a sleeve gastrectomy procedure. Flexible wire form 86 is advanced out of device 80 and into an internal surface of stomach "S." The flexibility of flexible wire form 86 enables flexible wire form 86 to curve into any suitable shape for remodeling a curvature of stomach "S." For example, flexible wire form 86 can be advanced against stomach "S" and curled to form a B-shape with a first looped portion 86a and a second looped portion 86b that cooperate to remodel the curvature of stomach "S" for resection. Stomach "S" can then be at least partially resected, as appropriate, separating the stomach "S" into a resected portion "R" and a new stomach portion "SN." Before completion of the resection, flexible wire form 86 can be withdrawn so that resection can be completed. Upon completion of the resection, the new stomach portion "SN" can be tested for extravasation as described above. The resected portion "R" can be grasped by a separate forceps and removed, and balloon 84 can be deflated so that device 80 can be withdrawn.

Figure 8:
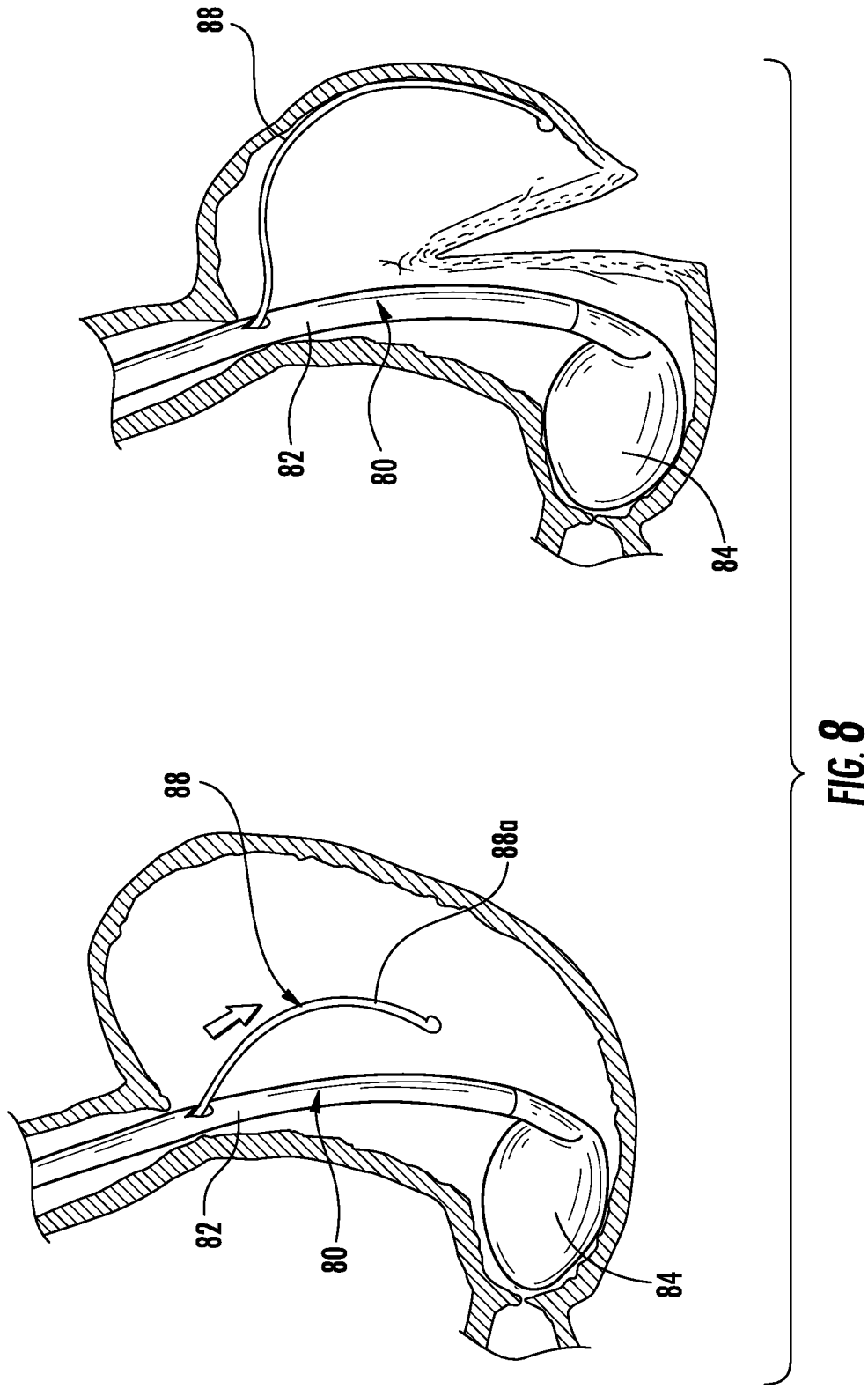

Turning now to FIG. 8, device 80 can include a rigid wire form 88 instead of flexible wire form 86. Rigid wire form 88 includes a curved distal end portion 88a that is advanced out of device 80 and against stomach "S" to remodel a curvature of stomach "S." Similar to that described above, stomach "S" can then be at least partially resected, as appropriate, separating the stomach "S" into a resected portion "R" and a new stomach portion "SN." Before completion of the resection, rigid wire form 88 can be withdrawn so that resection can be completed. Upon completion of the resection, the new stomach portion "SN" can be tested for extravasation as described above. The resected portion "R" can be grasped by a separate forceps and removed, and balloon 84 can be deflated so that device 80 can be withdrawn.

Figure 9:
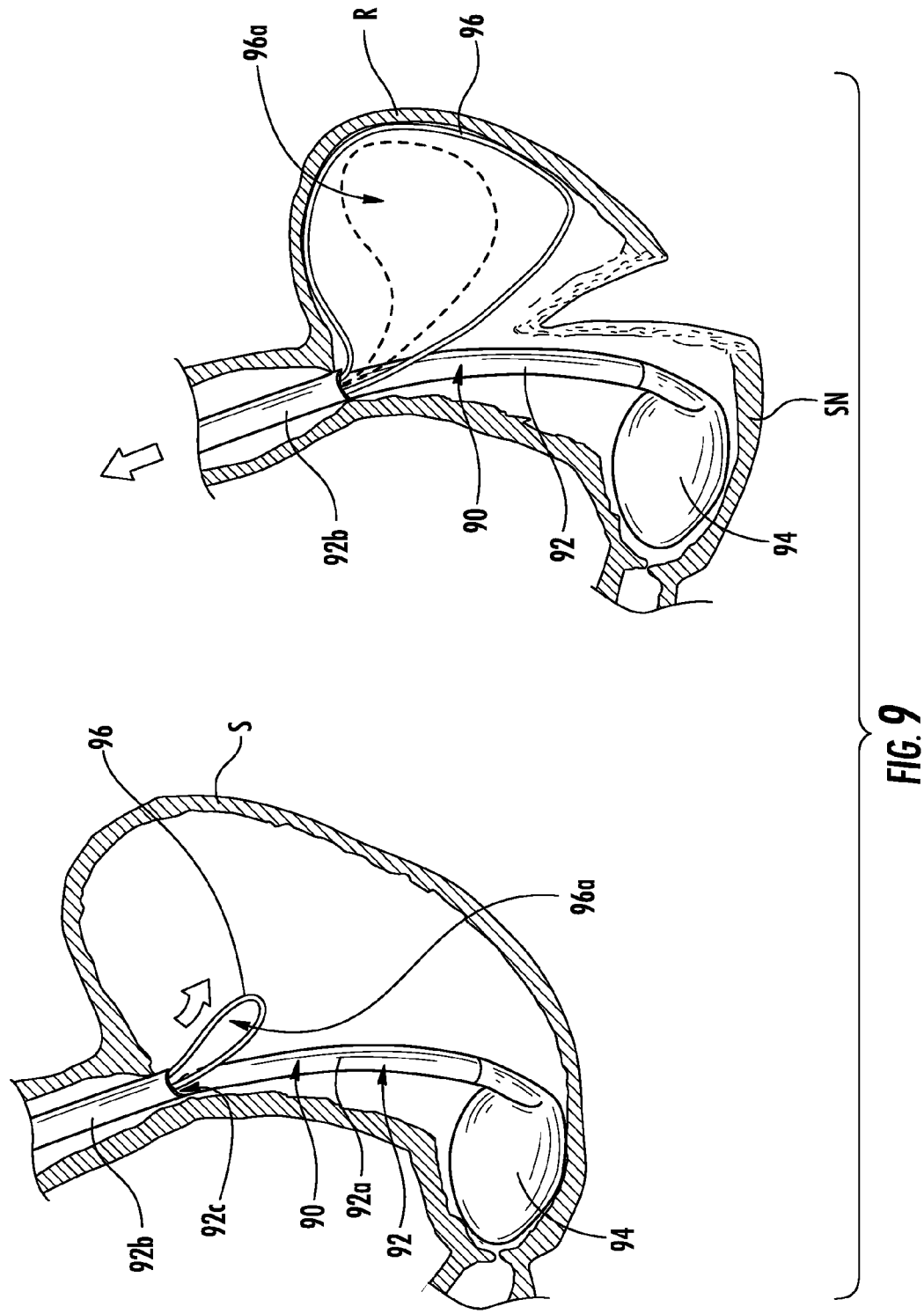

As seen in FIG. 9, one embodiment of a sleeve gastrectomy device is shown generally identified by reference numeral 90. Device 90 includes a tubular member 92 and an expandable balloon 94 supported on a distal end of tubular member 92. Tubular member 92 includes a distal end portion 92a and a proximal end portion 92b supported on distal end portion 92a. Proximal end portion 92b is positioned around distal end portion 92a to define a passage 92c therebetween that is dimensioned to receive a wire-forming loop 96.

Similar to balloon 14, balloon 94 is selectively inflated in the antrum of stomach "S" to position device 90 for effectuating a sleeve gastrectomy procedure. Wire forming loop 96 is advanced out of passage 92c and into an internal surface of stomach "S." Wire forming loop 96 defines a loop 96a that increases in diameter as wire-forming loop 96 is distally advanced from passage 92c and into contact with an internal surface of stomach "S" for remodeling the curvature of stomach "S" for resection. Stomach "S" can then be resected, as appropriate, while retracting wire-forming loop 96 to decrease the diameter of loop 96a as resection (e.g., stapling and cutting) progresses. The decrease in diameter of loop 96a may be indexed, for example, to correlate with the staple line formed in the stomach "S" during resection. The resection separates the stomach "S" into a resected portion "R" and a new stomach portion "SN." Before completion of the resection, Wire forming loop 96 can be withdrawn so that resection can be completed. Upon completion of the resection, the new stomach portion "SN" can be tested for extravasation as described above. The resected portion "R" can be grasped by a separate forceps and removed, and balloon 94 can be deflated so that device 90 can be withdrawn.

Figure 10:
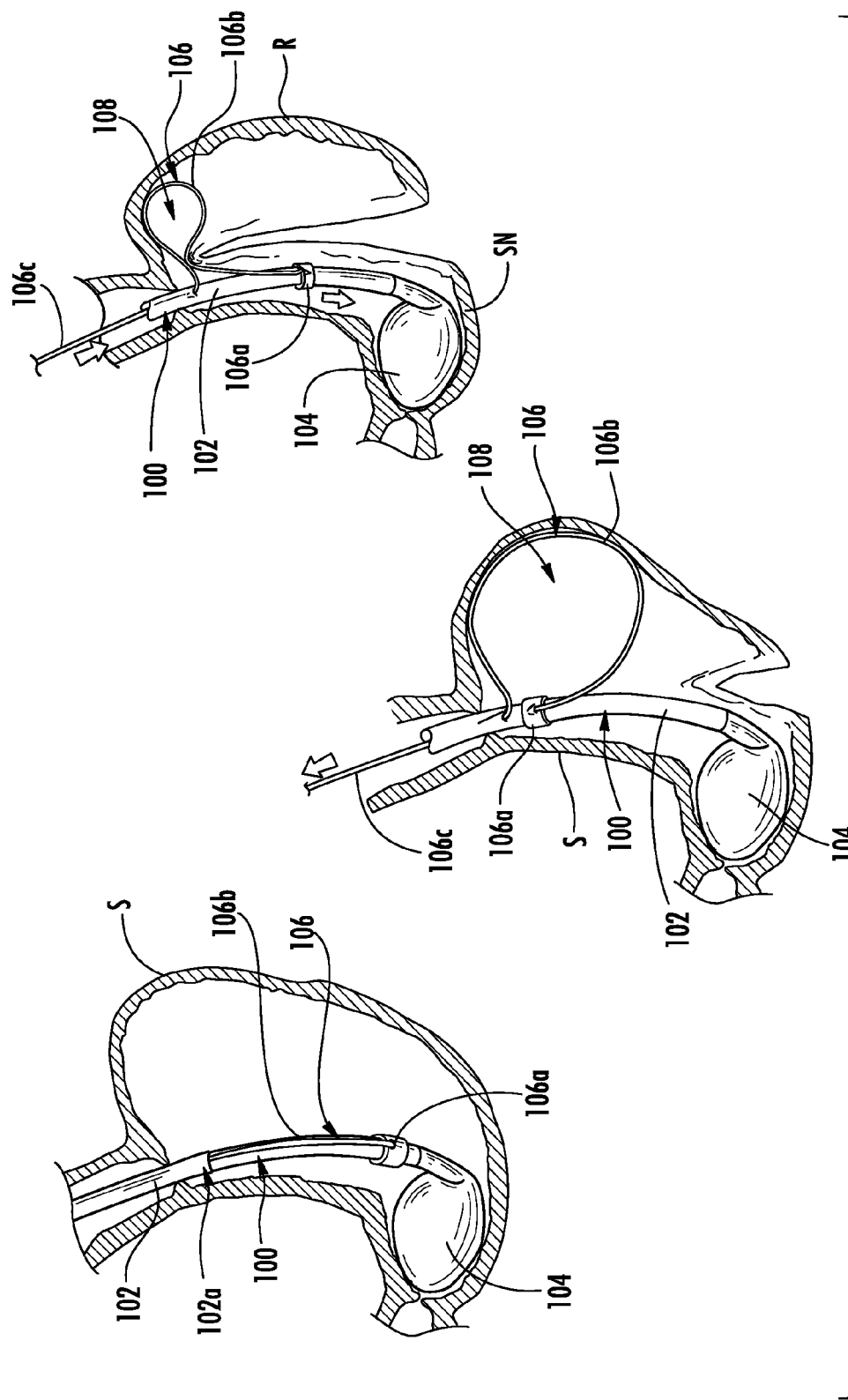

Turning now to FIG. 10, another embodiment of a sleeve gastrectomy device is shown generally identified by reference numeral 100. Device 100 includes a tubular member 102 and an expandable balloon 104 supported on a distal end of tubular member 102. Tubular member 102 defines an attachment point 102a and supports a loop collar 106 dimensioned to linearly translate about an outer surface of tubular member 102. Loop collar 106 includes a collar 106a, wire member 106b, and an actuation rod 106c. Wire member 106b extends along an outer surface of tubular member 102 and is secured to attachment point 102a at a proximal end of wire member 106b and to collar 106a at a distal end of wire member 106b. A distal end of actuation rod 106c is secured to collar 106a to move collar 106 linearly relative to tubular member 102 upon linear translation of actuation rod 106c. Actuation rod 106c extends along tubular member 102 and can be arranged to extend along the outer surface of tubular member 102 and/or through tubular member 102. Tubular member 102 can define a channel (not shown) therealong to facilitate linear movement of collar 106a.

Similar to balloon 14, balloon 104 is selectively inflated in the antrum of stomach "S" to position device 100 for effectuating a sleeve gastrectomy procedure. Actuation rod 106c is pulled proximally to draw collar 106a proximally. As collar 106a moves proximally relative to tubular member 102, wire member 106b extends outwardly forming a loop 108 that engages an internal surface of stomach "S" to remodel the curvature of stomach "S" for resection. Similar to that described above, stomach "S" can then be at least partially resected, as appropriate. As stapling and cutting progresses for the resection, actuation rod 106c can be distally advanced to distally advance collar 106a and tighten slack formed in wire member 106b as loop 108 decreases in diameter. Ultimately, collar 106a is advanced to a distal most position, e.g., the insertion position, so that wire 106b is flush or substantially flush against tubular member 102 so that loop 108 can be retracted for final stapling and cutting. Upon completion of the resection, the stomach "S" is resected into a resected portion "R" and a new stomach portion "SN" that can be tested for extravasation as described above. The resected portion "R" can be grasped by a separate forceps and removed, and balloon 104 can be deflated so that device 100 can be withdrawn.

Figure 11:
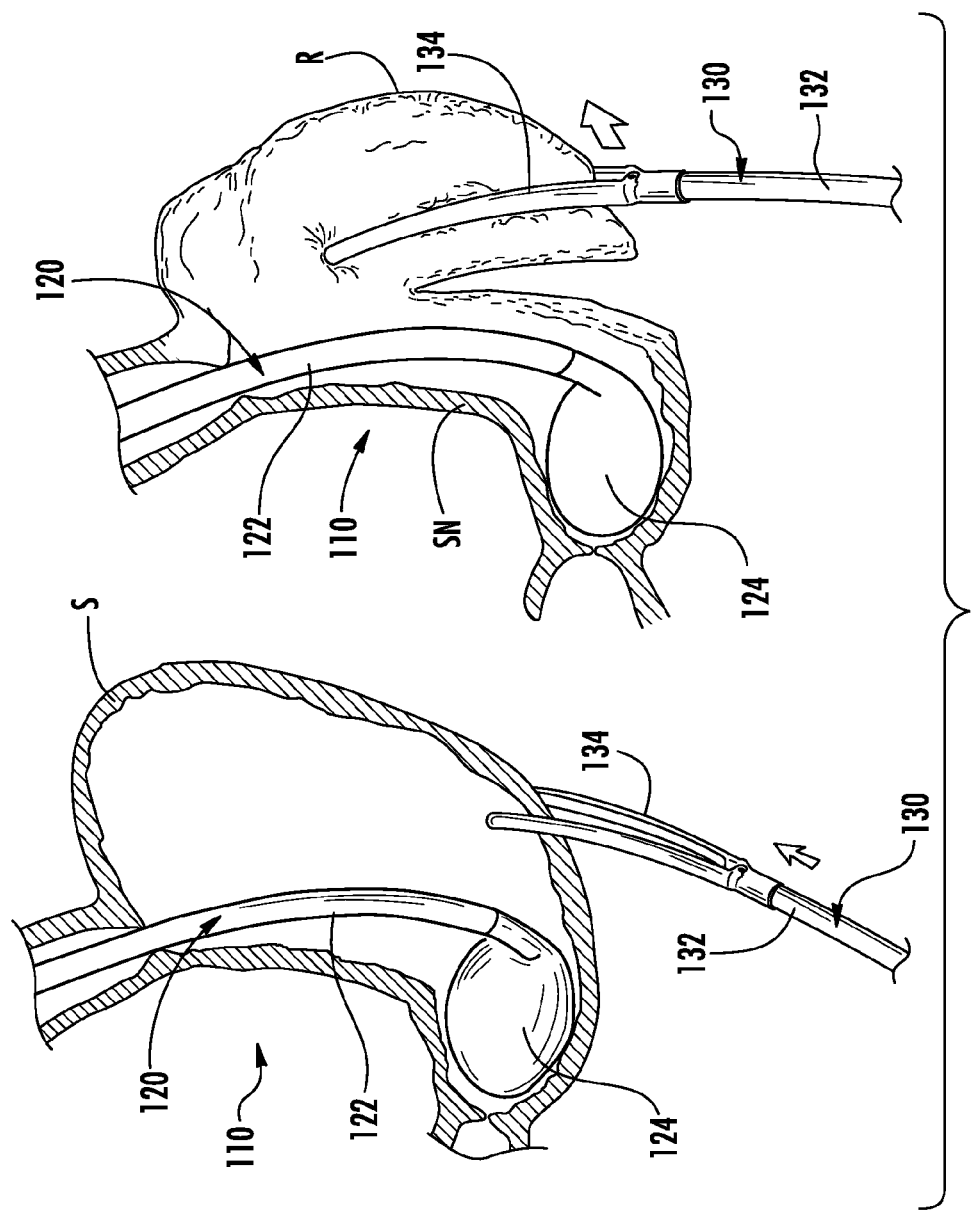

As seen in FIG. 11, an embodiment of a sleeve gastrectomy system is shown generally identified by reference numeral 110. System 110 includes a device 120 and grasping instrument 130. Device 120 includes a tubular member 122 and an expandable balloon 124 supported on a distal end of tubular member 122. Grasping instrument 130 includes an elongate body 132 and an end effector 134

Similar to balloon 14, balloon 124 is selectively inflated in the antrum of stomach "S" to position device 120 for effectuating a sleeve gastrectomy procedure. End effector 134 of grasping instrument 130 can be used to grasp a portion of stomach "S" to be removed upon resection. Similar to that described above, stomach "S" can then be resected into a resected portion "R" and a new stomach portion "SN." Upon completion of the resection, the new stomach portion "SN" can be tested for extravasation as described above. The resected portion "R" can be removed by grasping instrument 130, and balloon 104 can be deflated so that device 120 can be withdrawn.

Turning now to FIGS. 12-31, embodiments of tubular members of sleeve gastrectomy devices can include at least one expandable feature to facilitate securement of the respective embodiments of gastrectomy devices within the stomach, for example, within the antrum of the stomach.

Figure 12:
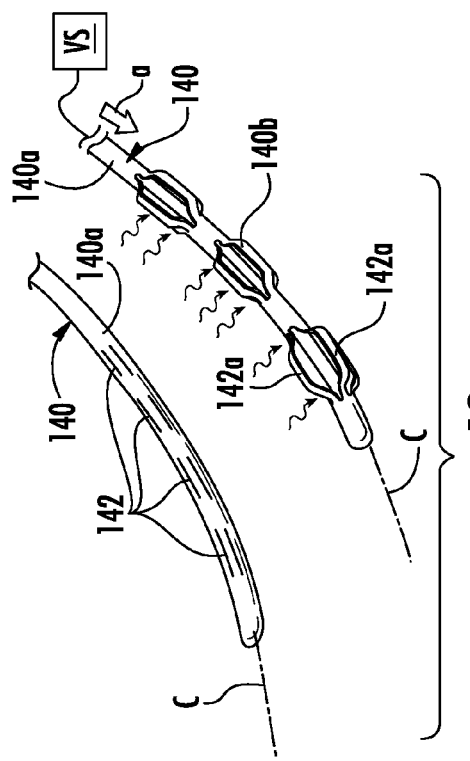

As shown in FIG. 12, one embodiment of a distal end portion of a tubular member is shown generally identified by reference numeral 140. Tubular member 140 includes an outer member 140a and an inner member 140b that defines a centerline "C." Outer member 140a includes a plurality of umbrella members 142 that are selectively expandable relative to centerline "C" between a contracted state and an expanded state in response to linear movement of outer member 140a relative to inner member 140b, as indicated by arrow "a." Each umbrella member 142 can have the same and/or different outer diameters in the contracted and/or expanded states and each umbrella member 142 includes a plurality of segments 142a that are positioned radially around tubular member 140. Each segment 142a of the plurality of segments 142a is spaced apart from the other segments 142a of the plurality of segments when umbrella member 142 is disposed in the expanded state and can be in contact with adjacent segments 142a when umbrella member 142 is in the contracted state. Tubular member 140 can be secured to vacuum source "VS" adapted to enable suction through one or more of the plurality of umbrella members 142 when in the expanded state.

Figure 13:
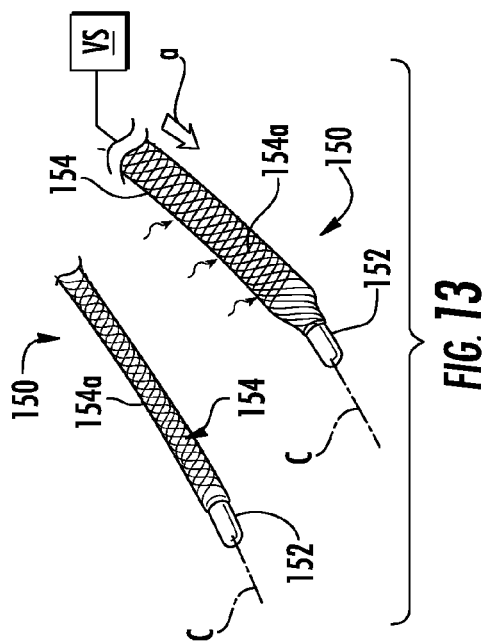

As depicted in FIG. 13, another embodiment of a distal end portion of a tubular member is shown generally identified by reference numeral 150. Tubular member 150 includes a shaft 152 and a polymer braid 154 with a plurality of braided filaments 154a secured to shaft 152. Shaft 152 defines a centerline "C." Braid 154 is selectively expandable relative to centerline "C" between a contracted state and an expanded state in response to linear movement of braid 154 relative to shaft 152, as indicated by arrow "a." Tubular member 150 can be secured to vacuum source "VS" adapted to enable suction between adjacent braided filaments 154a of braid 154 when braid 154 is in the expanded state.

Figure 14:
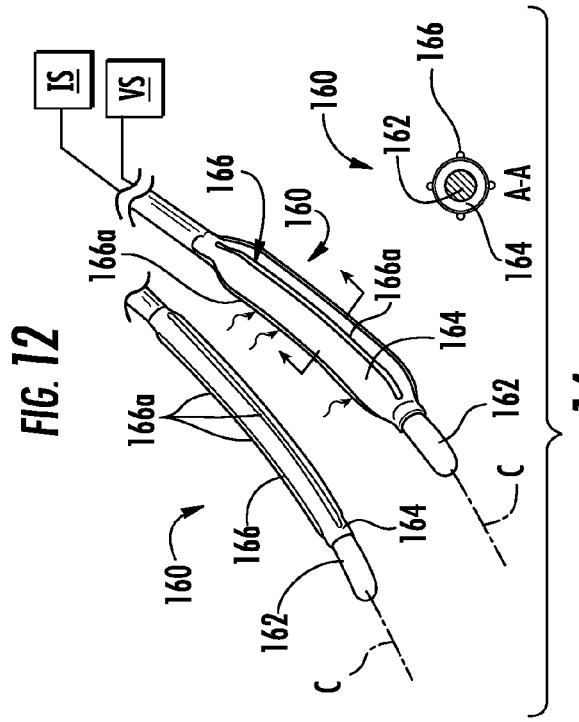

Turning now to FIG. 14, another embodiment of a distal end portion of a tubular member is shown generally identified by reference numeral 160. Tubular member 160 includes a shaft 162 that defines a centerline "C," a compliant balloon 164 supported on shaft 162, and a plurality of vacuum tubes 166 supported on balloon 164 and extending along shaft 162. Compliant balloon 164 can be coupled to an inflation source "IS" that is adapted to deliver inflation fluid, e.g., saline, to balloon 164 for selectively expanding and/or contracting balloon 164 between a contracted state and an expanded state relative to centerline "C." The plurality of vacuum tubes 166 defines a plurality of vacuum ports 166a. A vacuum source "VS" can be coupled to vacuum tubes 166 to provide suction through vacuum ports 166a.

As depicted in FIG. 15, another embodiment of a distal end portion of a tubular member is shown generally identified by reference numeral 170. Tubular member 170 includes a shaft 172 and a compliant balloon 174 supported on a side surface of shaft 172. Shaft 172 defines a centerline "C," a plurality of vacuum ports 172a, and vacuum lumen 172b that extends along centerline "C" and is in fluid communication with the plurality of vacuum ports 172a. A vacuum source "VS" can be coupled to vacuum lumen 172b to provide suction through vacuum ports 172a. Compliant balloon 174 is coupled to an inflation conduit 176 that extends along shaft 172 and can be coupled to an inflation source "IS" adapted to deliver inflation fluid, e.g., saline, to balloon 174 for selectively expanding and/or contracting balloon 174 between a contracted state and an expanded state relative to the side surface of shaft 172.

As seen in FIG. 16, yet another embodiment of a distal end portion of a tubular member is shown generally identified by reference numeral 180. Tubular member 180 includes a shaft 182 and a plurality of compliant balloons 184 supported in spaced-apart relation radially around an outer surface of shaft 182. Shaft 182 defines a centerline "C" and a plurality of vacuum ports 186 positioned between adjacent balloons 184 of the plurality of compliant balloons 184. The plurality of vacuum ports 186 includes a first port 186a, a second port 186b, and a third port 186c. Vacuum ports 186 are in fluid communication with a vacuum lumen 186d defined by shaft 182. Vacuum lumen 186d extends along centerline "C" of shaft 182. A vacuum source "VS" can be coupled to vacuum lumen 186d to provide suction through the plurality of vacuum ports 186. The plurality of compliant balloons 184 includes a first balloon 184a, a second balloon 184b, and a third balloon 184c. Each of the plurality of compliant balloons 184 is coupled to an inflation conduit 188 that extends along shaft 182 and can be coupled to an inflation source "IS" adapted to deliver inflation fluid, e.g., saline, to the balloons 184 for selectively expanding and/or contracting balloons 184 between a contracted state and an expanded state relative to the outer surface of shaft 182. A separate inflation conduit 188 can be coupled to each of first, second, and third balloons 184a, 184b, 184c.

Turning now to FIG. 17, another embodiment of a distal end portion of a tubular member is shown generally identified by reference numeral 190. Tubular member 190 includes a shaft 192 and an expandable coil 194 helically supported around an outer surface of shaft 192. A distal end of expandable coil 194 is secured to a distal end portion of shaft 192 Shaft 192 defines a centerline "C," and a plurality of vacuum ports 192a, and vacuum lumen 192b that extends along centerline "C" and is in fluid communication with the plurality of vacuum ports 192a. A vacuum source "VS" can be coupled to vacuum lumen 192b to provide suction through vacuum ports 192a. As indicated by arrow "a," expandable coil 194 can be linearly advanced along shaft 192 relative to centerline "C" for selectively expanding and/or contracting coil 194 between a contracted state, where coil 194 is adjacent to shaft 192, and an expanded state, where coil 194 is spaced from shaft 192. Adjacent turns of expandable coil 194 are closer to one another in the expanded state than in the contracted state, and vice versa.

As depicted in FIG. 18, another embodiment of a distal end portion of a tubular member is shown generally identified by reference numeral 200. Tubular member 200 includes an outer shaft 202a, an inner shaft 202b, and a rolling member 204 secured to a side surface of inner shaft 202b along an edge of rolling member 204. Inner shaft 202b defines a centerline "C" and a plurality of vacuum ports 206. In response to rotational movement of inner shaft 202b, for example, in the direction indicated by arrow "$b_1$," rolling member 204 is movable between a contracted state, where rolling member 204 is wrapped around inner shaft 202b in an overlapping arrangement in close proximity to the centerline "C," and an expanded state, where rolling member 204 is unraveled, for example in the direction indicated by arrow "$b_2$," so that portions of rolling member 204 are farther from centerline "C" than those respective portions are in the contracted state. A vacuum source "VS" can be coupled to vacuum ports 206, for example, via a vacuum lumen (not shown) to provide suction through vacuum ports 206.

As seen in FIG. 19, another embodiment of a distal end portion of a tubular member is shown generally identified by reference numeral 210. Similar to tubular member 200, tubular member 210 can include a plurality of spaced apart rolling members such as rolling members 204a-204d, etc.

As depicted in FIG. 20, still another embodiment of a distal end portion of a tubular member is shown generally identified by reference numeral 220. Tubular member 220 includes a shaft 222 and a plurality of spaced-apart balloons 224 that are selectively expandable relative to a centerline "C" defined by shaft 222 between contracted and expanded states. The plurality of balloons 224 can includes a first balloon 224a, a second balloon 224b, and a third balloon 224c, etc., each of which can be coupled to one or more inflation conduits (not shown) defined by shaft 222 that are in fluid communication with an inflation source "IS." Similar to that described above, shaft 222 defines a plurality of vacuum ports 222a in fluid communication with a vacuum source "VS," for example, via a vacuum lumen (not shown) defined by shaft 222 that couples to vacuum source "VS."

Turning now to FIG. 21, another embodiment of a distal end portion of a tubular member is shown generally identified by reference numeral 230. Tubular member 230 includes a shaft 232 that supports a self-expanding member 234 and a linearly translatable sheath 236 supported on self-expanding member 234. Sheath 236 is retractable in the direction indicated by arrow "a" to free self-expanding member 234 to enable self-expanding member 234 to expand from a contracted state, where sheath 236 covers self-expanding member 234, to an expanded state, where sheath 236 is retracted. Self-expanding member 234 can be formed of a shape memory material such as nitinol and/or an electroactive polymer.

Figure 22:
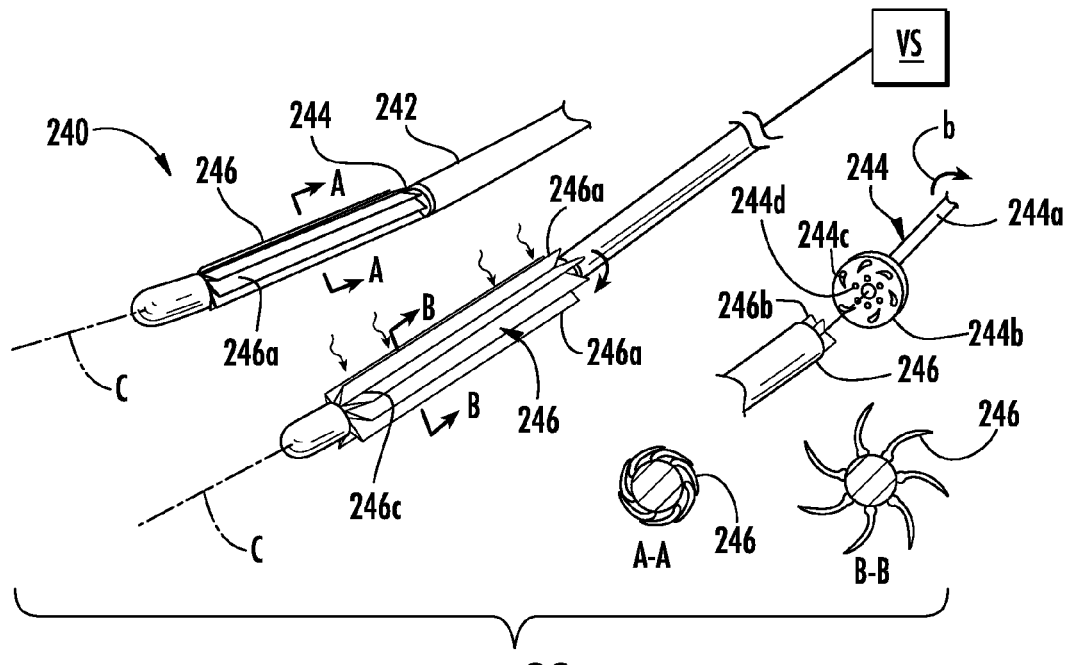

As seen in FIG. 22, still another embodiment of a distal end portion of a tubular member is shown generally identified by reference numeral 240. Tubular member 240 includes a shaft 242 that defines a centerline "C" and supports an actuating assembly 244 and a blade assembly 246. Actuating assembly includes drive shaft 244a that supports an actuator face 244b on a distal end of drive shaft 244a. Actuator face 244b defines a plurality of channels 244c and a plurality of passages 244d. Blade assembly 246 includes a plurality of blades 246a and defines vacuum ports 246c between each blade 246a of the plurality of blades 246a. Each blade 246a of the plurality of blades 246a includes a finger 246b extending proximally from a proximal end portion of blade 246a. Each finger 246b is received within one of the plurality of channels 244c so that rotational movement of actuation assembly 244, for example, in the direction indicated by arrow "b," rotates actuator face 244b so that fingers 246b of each blade 246a slide through channels 244c to rotate blade assembly 246 between expanded and contracted states relative to centerline "C." Vacuum ports 246c are in fluid communication with passages 244d, which can be coupled to a vacuum source "VS," as described above.

Figure 23:
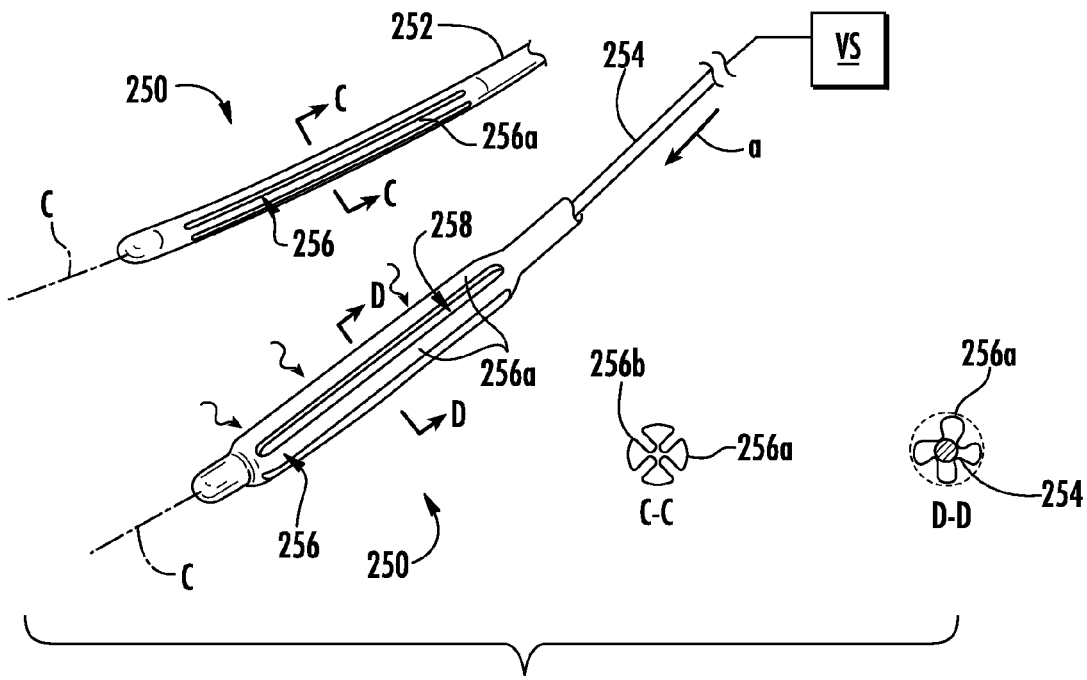

As seen in FIG. 23, another embodiment of a distal end portion of a tubular member is shown generally identified by reference numeral 250. Tubular member 250 includes an outer shaft 252, an inner shaft 254 supported within outer shaft 252, and a clover member 256 supported on outer shaft 252. Inner shaft 254 defines a centerline "C." Clover member 256 includes a plurality of radially spaced-apart clovers 256a and defines a central lumen 256b. Inner shaft 254 is linearly translatable relative to outer shaft 252, as indicated by arrow "a," into central lumen 256b of clover member 256 so that the plurality of clovers 256a expands radially outwardly relative to the centerline "C" from a contracted state to an expanded state. Clover member 256 defines a plurality of vacuum ports 258 between the plurality of clovers 256a. Similar to that described above, vacuum ports 258 are in fluid communication with a vacuum source "VS" coupled to tubular member 250 at a proximal end portion thereof.

Turning now to FIG. 24, another embodiment of a distal end portion of a tubular member is shown generally identified by reference numeral 260. Tubular member 260 includes an inner shaft 262 that defines a centerline "C" and supports a plurality of stacked outer shafts 264 that are linearly translatable along centerline "C," as indicated by arrow "a" in a telescoping arrangement. The plurality of stacked outer shafts 264 can include a first outer shaft 264a, a second outer shaft 264b, and a third outer shaft 264c, etc., where each outer shaft has a different outer diameter with each successive outer diameter increasing in size so that tubular member 260 can expand from a contracted state, which can be defined by the diameter of the outer surface of inner shaft 262, to an expanded state, which can be defined the diameter of the outer surface of one of the plurality of stacked outer shafts 264. Any of the inner and/or outer shafts 262, 264 can define a plurality of vacuum ports 266 that can be disposed in fluid communication with a vacuum source "VS" as described above.

As seen in FIG. 25, one embodiment of a distal end portion of a tubular member is shown generally identified by reference numeral 270. Tubular member 270 includes a shaft 272 that defines a centerline "C," a balloon member 274 supported on shaft 272 in fluid communication with an inflation source "IS," and a foam member 276 supported on balloon member 274 that expands from a contracted state to an expanded state in response to inflation of balloon member 274 via inflation source "IS." Foam member 276 is in fluid communication with one or more vacuum conduits 278 that are coupled to a vacuum source "VS" similar to that described above.

With reference to FIG. 26, another embodiment of a distal end portion of a tubular member is shown generally identified by reference numeral 280. Tubular member 280 includes an outer shaft 282 that defines a central lumen 282a and a centerline "C" and includes a low durometer distal portion 282b. Tubular member 280 supports a plurality of rods 284 that can be linearly advanced along centerline "C," as indicated by arrow "a," into a distal end portion of central lumen 282a to expand distal portion 282b of outer shaft 282 from a contracted state to an expanded state. Outer shaft 282 can define a plurality of vacuum ports 286 that are in fluid communication with a vacuum source "VS" as described above.

Turning now to FIG. 27, another embodiment of a distal end portion of a tubular member is shown generally identified by reference numeral 290. Tubular member 290 includes a shaft 292 that defines a centerline "C," a plurality of expandable members 294, a plurality of rigid collars 296 interleaved between the plurality of expandable members 294, and an actuation rod 298 secured to a distal tip 292a of shaft 292. Actuation rod 298 is linearly translatable relative to centerline "C," as indicated by arrow "a" to compress expandable members 294 against rigid collars 296 thereby expanding expandable members 294 from a contracted state to an expanded state. Collars 296 can define vacuum ports 296a that are in fluid communication with a vacuum source "VS," similar to that described above.

As seen in FIG. 28, another embodiment of a distal end portion of a tubular member is shown generally identified by reference numeral 300. Tubular member 300 includes a shaft 302 that defines a centerline "C" and vacuum lumen 302a in fluid communication with a vacuum source "VS" as described above. Shaft 302 supports a plurality of inner shafts 304, each of the plurality of inner shafts 304 includes a curved portion 304a. Each inner shaft 304 of the plurality of inner shafts 304 is rotatable, as indicated by arrows "b," so that curved portions 304a rotate between a contracted state, where curved portions 304a are inwardly directed, to an expanded state, where curved portions 304a are outwardly directed.

With reference to FIG. 29, another embodiment of a distal end portion of a tubular member is shown generally identified by reference numeral 310. Tubular member 310 includes an outer shaft 312a that defines a centerline "C" and an inner shaft 312b that supports a clamshell assembly 314. One or both of inner and outer shafts 312a, 312b can define one or move vacuum ports (not shown) that are in fluid communication with a vacuum source "VS" similar to that described above. Clam shell assembly 314 includes a first shell 314a and second shell 314b that are pivotally coupled to an actuation rod 316 at pivot 314c so that a rotational movement of actuation rod 316, as indicated by arrow "b," moves clam shell assembly 314 between a contracted state, where first and second shells 314a, 314b are in close approximation with centerline "C," and an expanded state, where first and second shells 314a, 314b are spaced from centerline "C."

Figure 30:
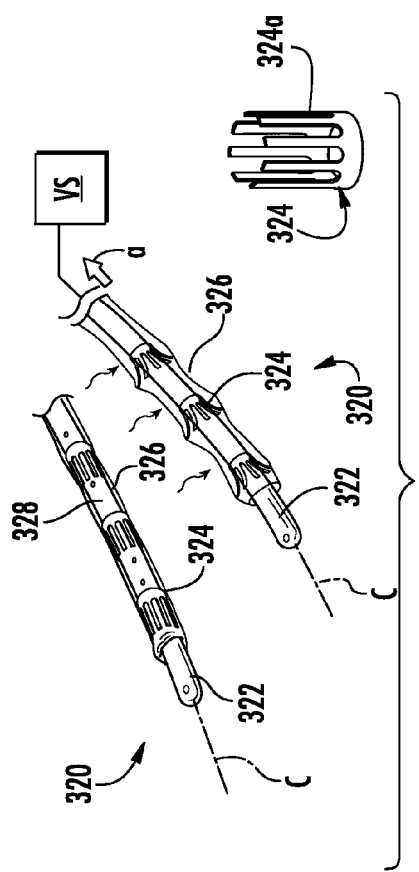

Turning now to FIG. 30, another embodiment of a distal end portion of a tubular member is shown generally identified by reference numeral 320. Tubular member 320 includes a shaft 322 that defines a centerline "C," a plurality of laser cut tubes 324 disposed on shaft 322, and a sheath 326 secured to the plurality of laser cut tubes 324 that is linearly movable relative to the plurality of laser cut tubes 324, as indicated by arrow "a." Sheath 326 can define a plurality of vacuum ports 328 that are in fluid communication with a vacuum source "VS" similar to that described above. Each tube of the plurality of laser cut tubes 324 includes a plurality of tines 324a disposed radially about the tube 324. Each tine of the plurality of tines 324a is secured to sheath 326 so that linear movement of sheath 326 moves tines 324a between a contracted state, where tines 324a and sheath 326 are in close proximity to centerline "C" and an expanded state, where tines 324a and sheath 326 are radially spaced from centerline "C."

Figure 31:
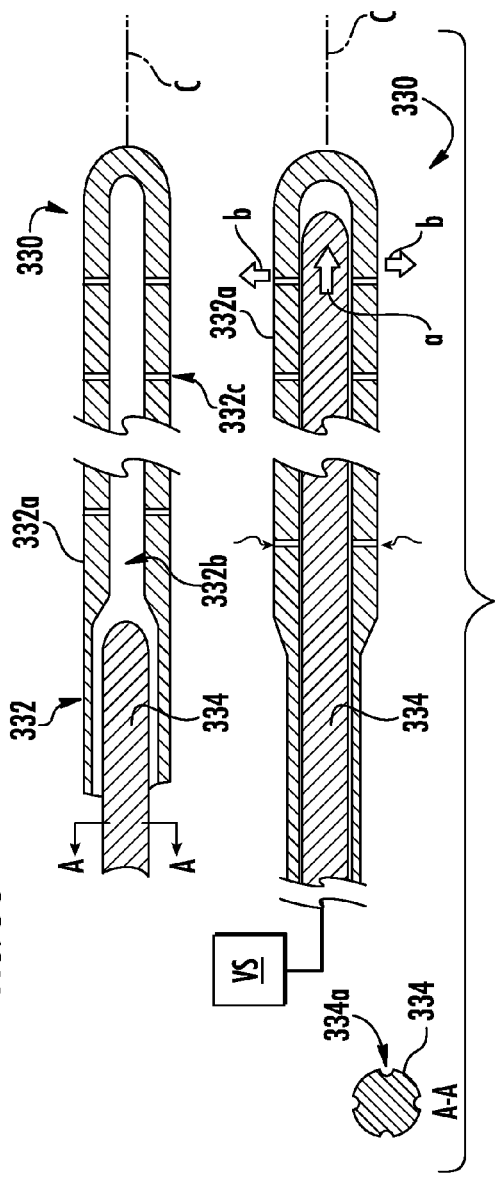

As seen in FIG. 31, still another embodiment of a distal end portion of a tubular member is shown generally identified by reference numeral 330. Tubular member 330 includes a shaft 332 has an expandable portion 332a and defines a centerline "C," a central lumen 332b, and a plurality of vacuum ports 332c. Shaft 332 supports a mandrel 334 that is linearly movable through central lumen 332b, as indicated by arrow "a," to move expandable portion 332a between a contracted state and an expanded state, as indicated by arrows "b." Mandrel 334 defines a plurality of flutes 334a that extend along a length of mandrel 334 to provide a fluid communication between vacuum ports 332c and a vacuum source "VS" coupled to a proximal end portion of tubular member 330, as described above.

FIGS. 32-41 are views illustrating various embodiments of gastrectomy devices including stapling location identifying features.

With reference to FIG. 32, device 120, described above, is shown with balloon 124 thereof inflated to fill antrum of stomach "S" to give a visual start indicator "I" for identifying a stapling location, which is shown, for example, at 6 centimeters. As can be appreciated, balloon 124 can be filled with any suitable biocompatible filler including, for example, air, saline, and/or foam.

As seen in FIG. 33, embodiments of gastrectomy devices, such as device 340, can include a shaft 340a defining a channel 340b and supporting a pivoting foot 340c on a distal end portion of shaft 340a. Device 340 is adapted to receive a rigid rod 342 that can be advanced through channel 340 to engage and pivot pivoting foot 340c about pivot 340d, as indicated by arrow "a." Alternatively, or additionally, a suture 344 can be received in channel 340 that is secured to a proximal end of pivoting foot 340c to pivot pivoting foot 340c about pivot 340d by pulling suture 344, as indicated by arrow "b." In these embodiments, pivoting foot 340c can be positioned in stomach "S" to give a visual start indicator "I," as described above.

Figure 34:
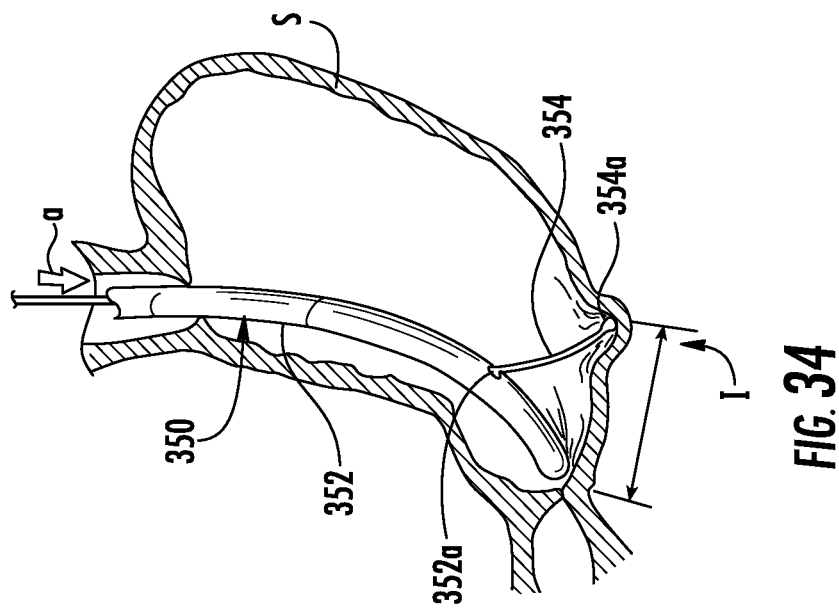

With reference to FIG. 34, embodiments of gastrectomy devices, such as device 350, can include a shaft 352 defining an aperture 352a and supporting a wire form probe 354 that can be advanced out of aperture 352a so that a dimple 354a disposed on an end of probe 354 can engage an internal surface of stomach "S" to establish a visual start indicator "I," as described above.

Figure 35:
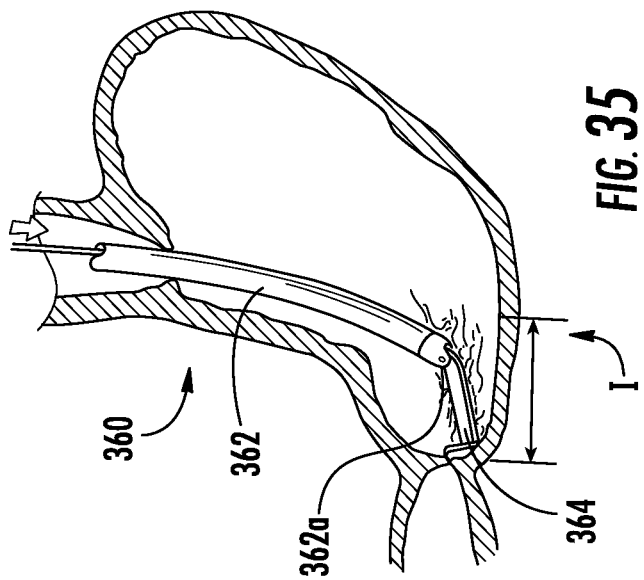

Turning now to FIG. 35, embodiments of gastrectomy devices, such as device 360, can include a shaft 362 defining an channel 362a and supporting a tape probe 364 that can be advanced out of channel 362a so that probe 364 can engage an internal surface of stomach "S" to establish a visual start indicator "I," as described above.

As seen in FIGS. 36 and 37, embodiments of gastrectomy devices, such as device 370 and device 380 can include similar features. For example, device 370 includes a distal positioning basket 372 and device 380 includes a distal positioning pigtail 382, each of which can serve to establish a visual start indicator "I," as described above.

Figure 38:
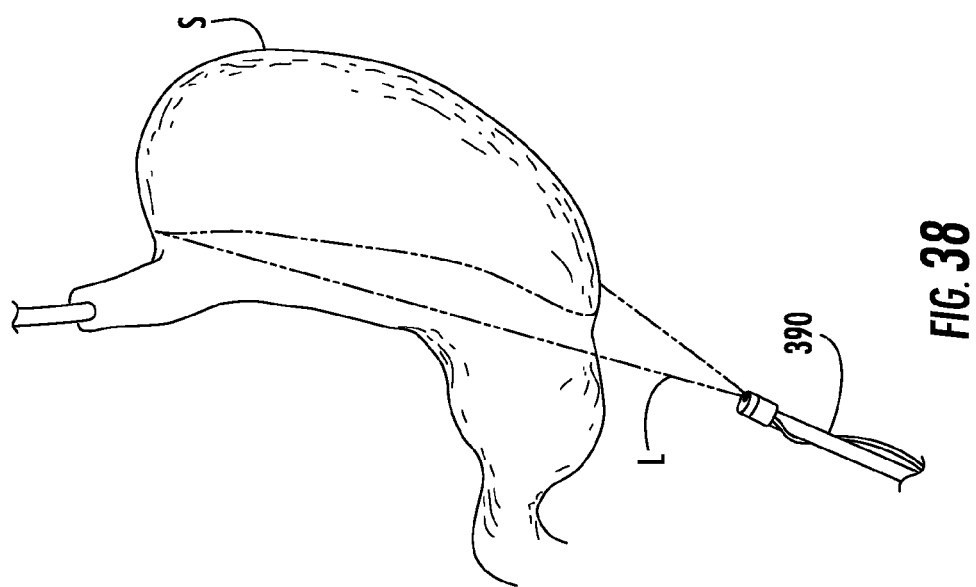

With reference to FIG. 38, embodiments of gastrectomy devices can be utilized with additional instruments such as a laser device 390 that is adapted to provide a projected staple line with the laser "L."

Figure 39:
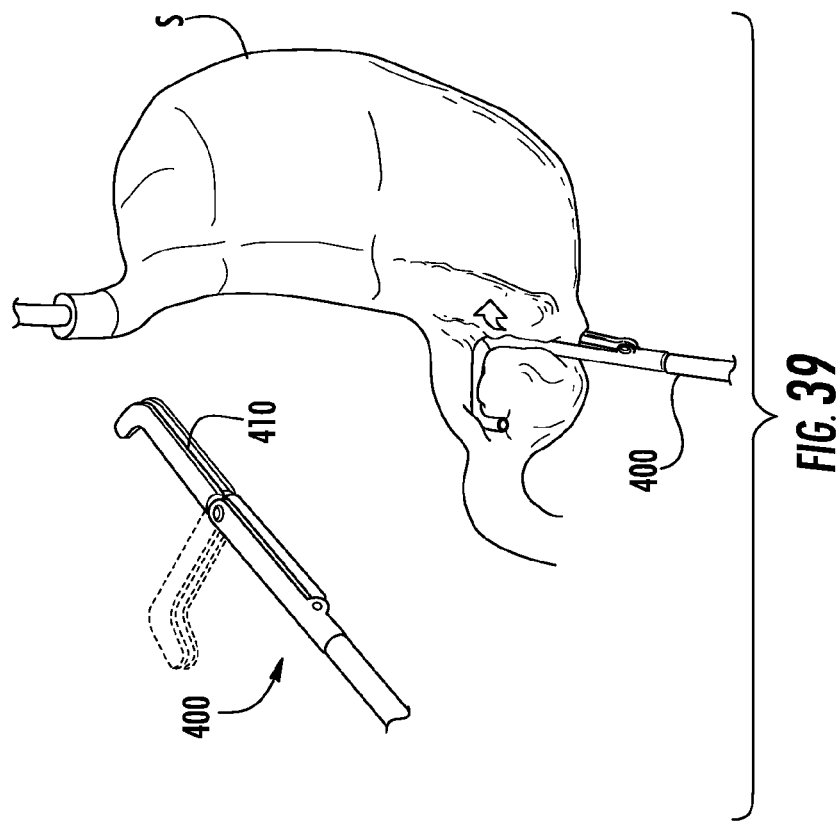

As depicted in FIG. 39, embodiments of gastrectomy devices can be utilized with additional instruments such as external position clamp 400. Clamp 400 can include a pivotable clamp 410 that is adapted to position an embodiment of a gastrectomy device in desired position in stomach "S" such as the antrum.

Figure 41:
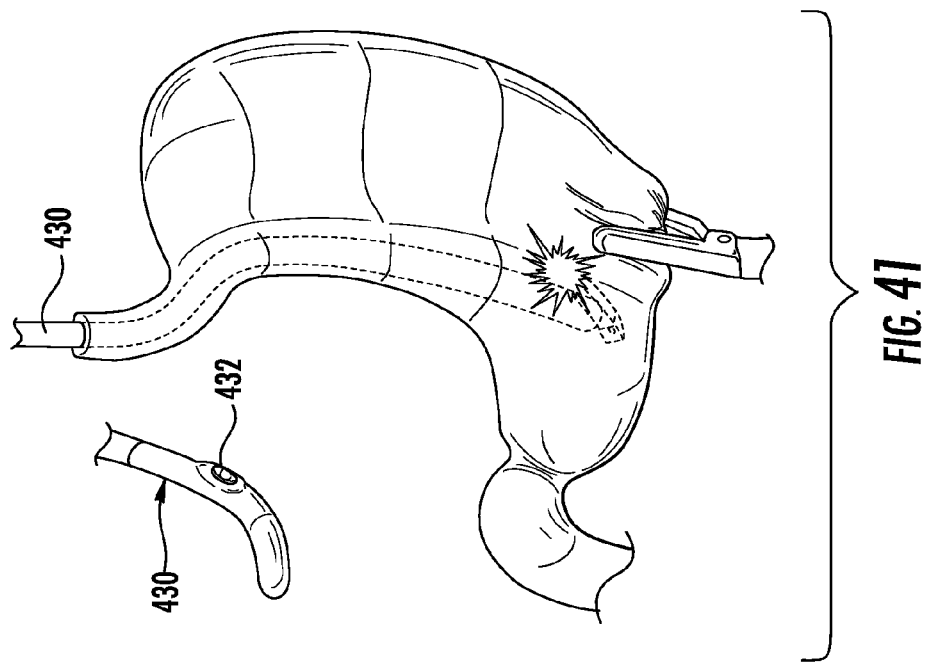
Figure 40:
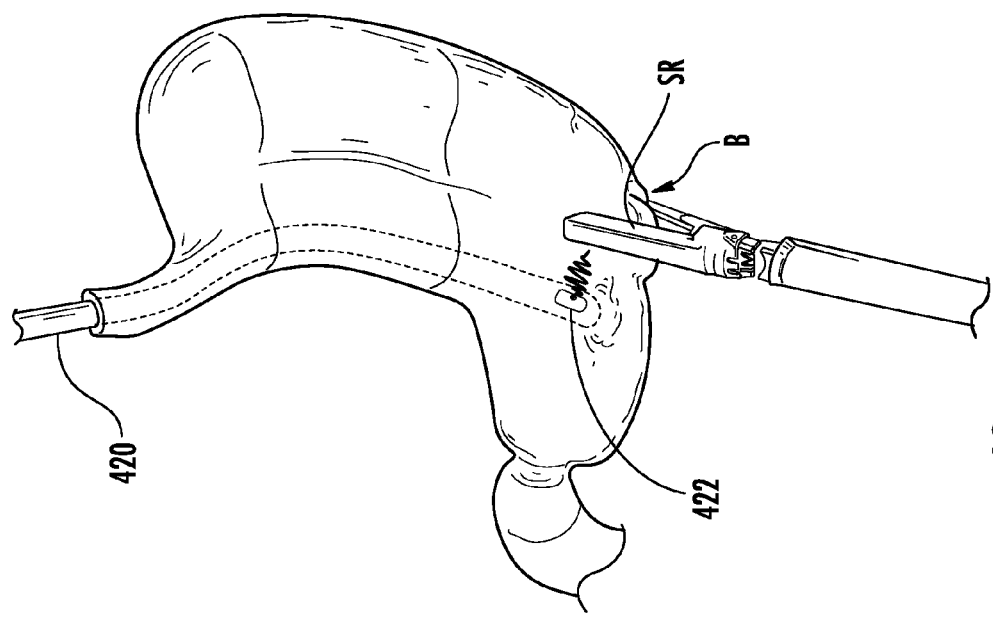

Turning now to FIGS. 40 and 41, embodiments of gastrectomy devices, such as device 420 and device 430 can also include features to help establish a visual start indicator. For example, device 420 includes an indicator device 422 such as an RF tag and/or a magnet that can communicate with a stapler relay "SR" to help identify a start position. Similarly, device 430 includes an LED indicator 432.

Figure 42:
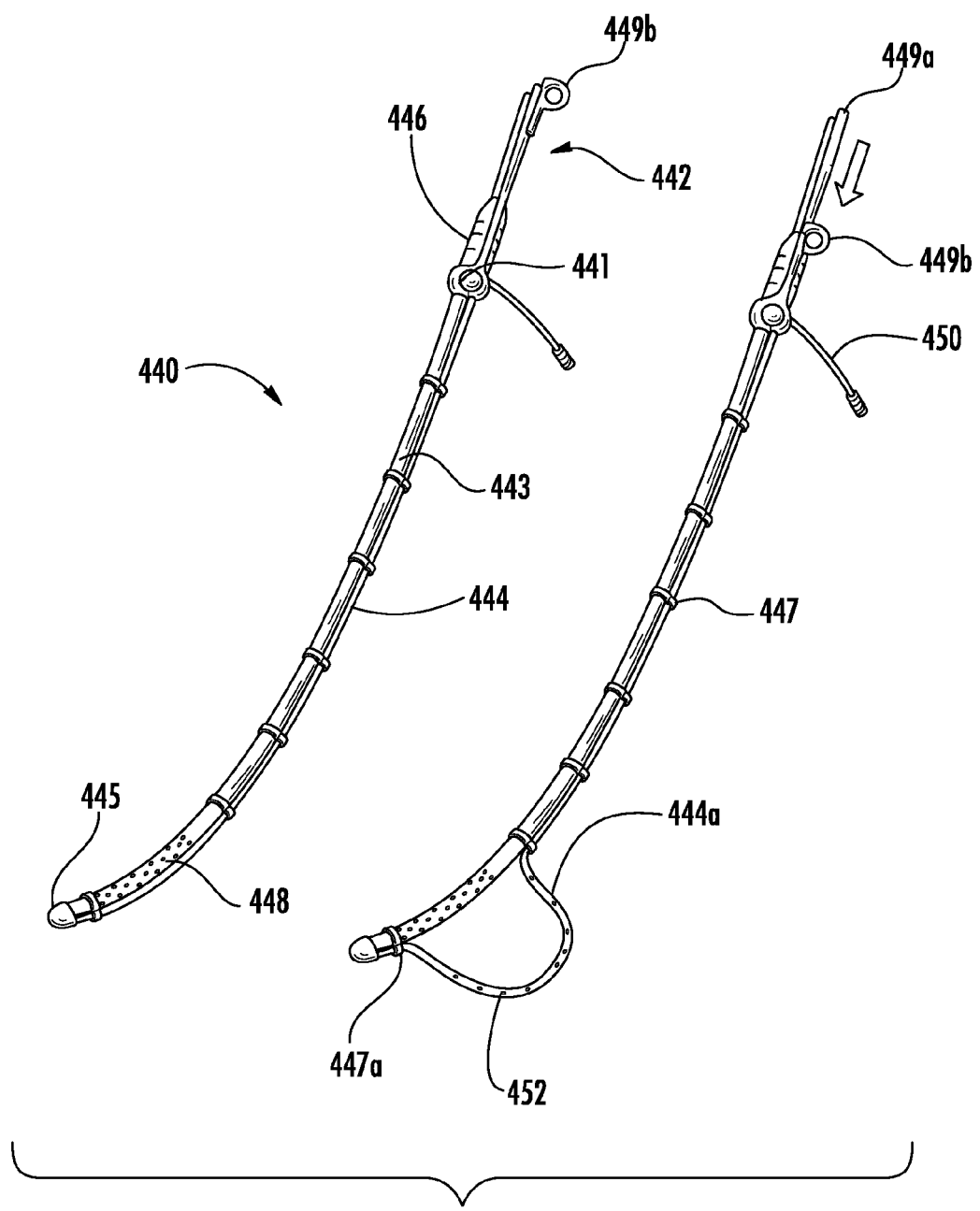
FIG. 42 shows a pair of perspective views of one embodiment of a gastrectomy device, one of the pair of perspective views showing the gastrectomy device in a first state, the other of the pair of perspective views showing the gastrectomy device in a second state.

With reference to FIG. 42, another embodiment of a gastrectomy device is shown generally identified by reference numeral 440 which is a device for the purpose of predictably remodeling the anatomy of the stomach, particularly the greater curvature, such that the approximated anterior and posterior sides of the stomach are uniform during partial sleeve gastrectomy with repeatable results from case to case. Device 440 features a proximal handle assembly 442 connected to a flexible polymer main shaft 443 with a second more rigid polymer deflection shaft 444 positioned parallel to and tangent to polymer shaft 443. The length of the deflection shaft 444 is such that it connects proximally to the actuating member 446 of the handle assembly 442 and distally to the atraumatic polymer tip 445; both the main shaft 443 and deflection shaft 444 being attached to the atraumatic tip 445 fully distal. The design of both the main shaft 443 and deflection shaft 444 are each tubes of specific outer diameters and wall thicknesses, respectively. In order to achieve ease of actuation and a specific curvature of the deflection shaft 444, relief features may be included of depth and pattern to affect the necessary deployed geometry.

A plurality of coupling brackets 447 exist along the length of the main shaft 443 in order to maintain the position of the main shaft 443 to the deflection shaft 444 over the length of the device. The connection of the coupling brackets 447 are such that they are mounted securely to the main shaft 443 while allowing the deflection shaft 444 to move freely, linearly. The location of a coupling bracket 447a dictates the resultant shape of the deflection shaft arc, and therefore can be spaced and positioned in a location(s) to maximize the effectiveness of the bow. A plurality of through lumens 448 in the main shaft exists at a specific distance from the distal end of the device over a specific length, and is oriented radial and perpendicular to the major axis of the shaft. The proximal handle assembly 442 includes a rigid, static handle 449a and a rigid, dynamic actuating member 449b. This actuating member 449b is attached to the static handle 449a in such a way as to be able to translate linearly over a specific distance. The deflection shaft 444 being attached to the actuation member 449b, when translating from proximal to distal, advances through the coupling brackets 447 distally. The result is that as the deflection shaft 444 is loaded in compression, being constrained by the static length of the main shaft 443, and bows into an arc 444a at the distal end of the device.

Within the handle assembly is a pressure regulator 441 that is linked to the inner lumen of the main shaft 443 through a lumen in the handle 442. A luer assembly 450 is also attached to the pressure regulator 441 in the handle 442 such that air can be introduced through the inner lumen of the main shaft 443 and through the lumens at the distal end 448 to achieve insufflation, or air withdrawn through this same path to achieve suction, both flow rates being controlled by the regulator 441. A length of LED lights 452 is housed within the ID of the deflection shaft 444 at the distal end of the device existing between the atraumatic tip 445 and the distal most coupling bracket 447*a*.

Figure 43:
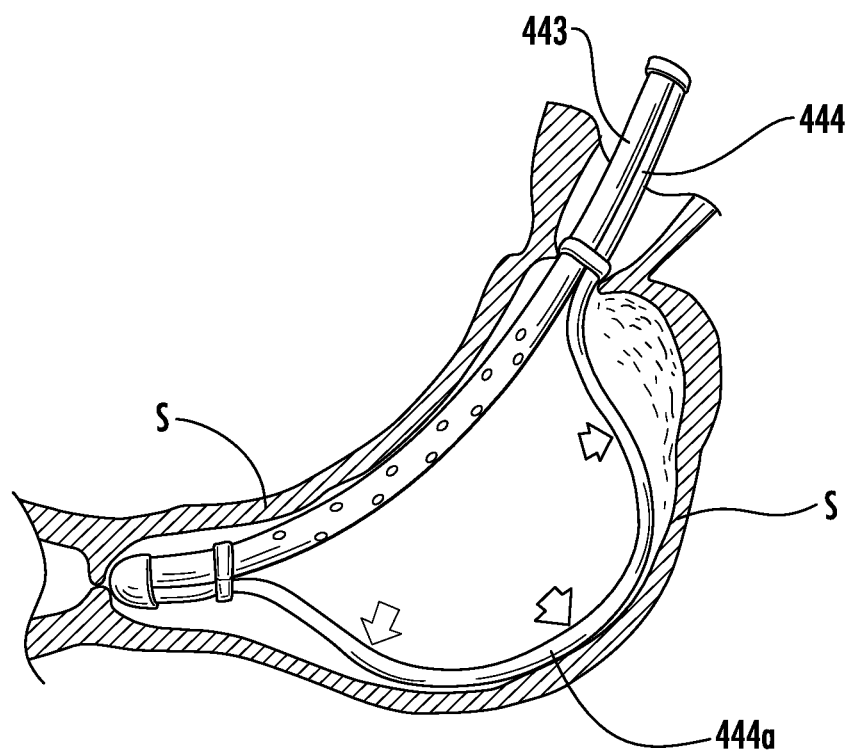
FIG. 43 shows a distal end portion of the gastrectomy device of FIG. 42 in the second state in a patient's stomach.

Referring to FIG. 43, in use, the main shaft 443 of the device is introduced into the patient through the mouth, down the esophagus, cannulating the esophageal sphincter, and placed distally at the area of the antrum and pylorus. The user then orients the device rotationally via the proximal handle such that the main shaft 443 is oriented against the inner curve of the stomach "S" and the deflection shaft 444 is oriented toward the greater curve of the stomach. The actuation member on the handle assembly is then advanced distally, activating the LED light array and resulting in the bowing effect of the deflection shaft to the degree that the arc 444*a* of the shaft interfaces with the greater curve, putting the anterior and posterior sides of the stomach in tension and uniform about the distal geometry of the device. The LED array creates a visual indicator to the surgeon of the placement of the bowed deflection shaft. Additionally, this deflection results in a resultant force causing the atraumatic distal end of the main shaft 443 to conform to the angularis and antrum. Suction is then applied through the main shaft 443, pulling the inner surfaces of the lesser curve against the perforated distal length of the main shaft 443 and deflating the stomach "S." This vacuum results in making the remodeled stomach static, to which the handle actuation member can be returned to its fully proximal position, retracting the bow of the deflection member and returning it tangent to the main shaft 443. As the main shaft 443 exists from the antrum, along the lesser curve, to the cardia, it serves as a visual template to the surgeon performing the resection procedure laparoscopically. This, along with the LED array, is a visual guide for application of the staple line over the resected stomach. Once the resection is completed, the device allows for pressure testing of the newly remodeled sleeve by ceasing suction and allowing for insufflation of the sleeve cavity to a specific pressure. Upon completion of the procedure, the device is removed from the patient. This LED array feature can be included as an element in any of the embodiments.

Figure 44:
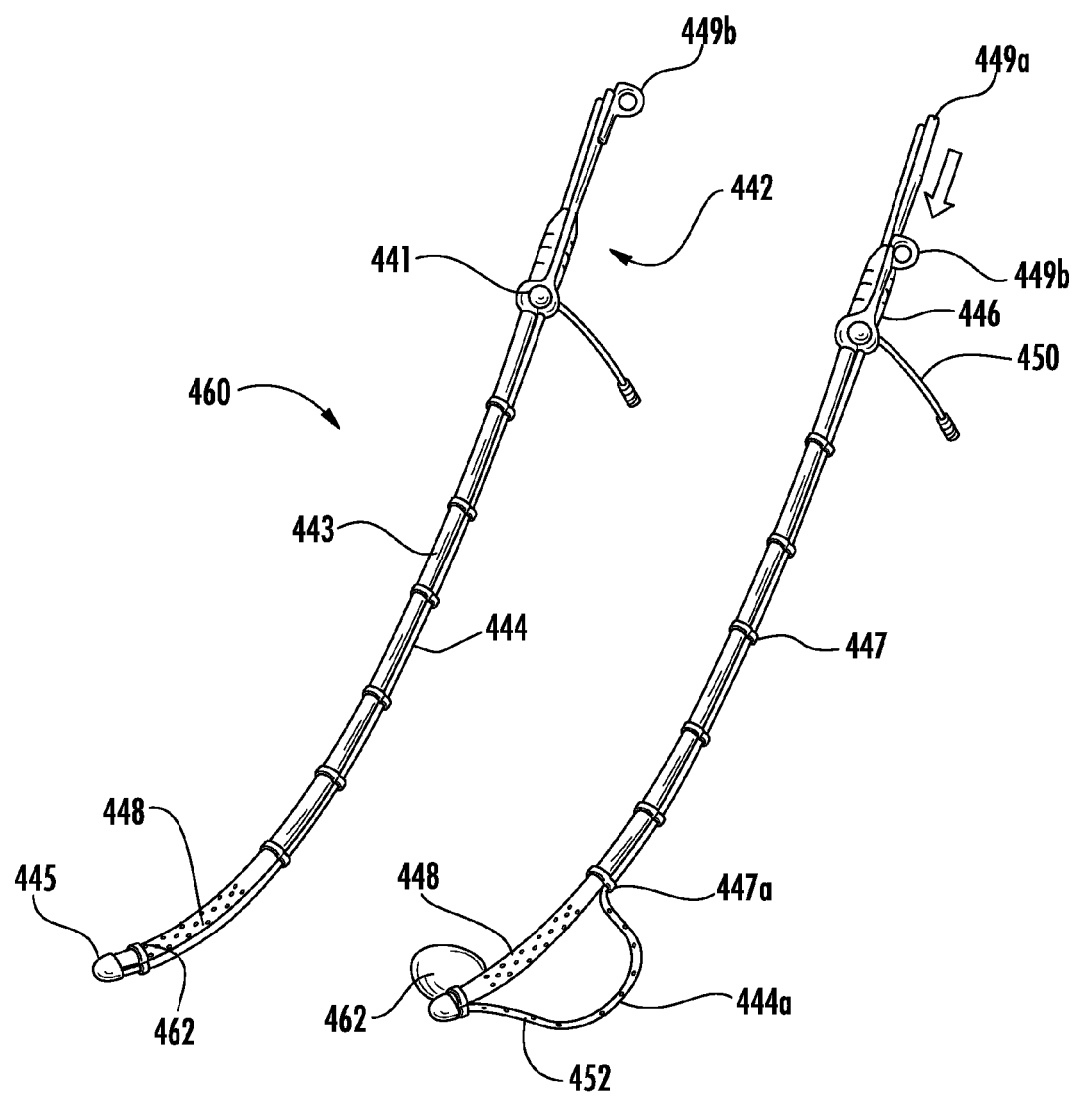
FIGS. 44 and 45 show perspective views of various embodiments of gastrectomy devices in first and second states.

With reference to FIG. 44, one embodiment of a gastrectomy device is shown generally identified by reference numeral 460 which similar to device 440 but includes a compliant balloon feature 462 is located at the distal end of the device and can be inflated via a lumen that runs from the handle, through the ID of the main shaft 443 to the balloon.

In use, the main shaft 443 of the device is introduced into the patient through the mouth, down the esophagus, cannulating the esophageal sphincter, and placed distally at the area of the antrum and pylorus. The user then orients the device rotationally via the proximal handle such that the main shaft 443 is oriented against the inner curve of the stomach and the deflection shaft is oriented toward the greater curve of the stomach. The actuation member 449*b* on the handle assembly 442 is then advanced distally, resulting in the bowing effect of the deflection shaft to the degree that the arc 444*a* of the shaft interfaces with the greater curve, putting the anterior and posterior sides of the stomach in tension and uniform about the distal geometry of the device. Additionally, this deflection results in a resultant force causing the atraumatic distal end of the main shaft 443 to conform to the angularis and antrum. The distal balloon 462 is then inflated to a specific volume that results in the balloon filling the antrum and positioning the distal end of the device a specific distance from the pylorus. This is the starting point to begin resection. Suction is then applied through the main shaft 443, pulling the inner surfaces of the lesser curve against the perforated distal length of the main shaft 443 and deflating the stomach. This vacuum results in making the remodeled stomach static, to which the handle actuation member 449*b* can be returned to its fully proximal position, retracting the arc 444*a* of the deflection member 444 and returning it tangent to the main shaft 443. As the main shaft 443 exists from the antrum, along the lesser curve, to the cardia, it serves as a visual template to the surgeon performing the resection procedure laparoscopically. Once the resection is completed and the balloon 462 deflated, the device allows for pressure testing of the newly remodeled sleeve by ceasing suction and allowing for insufflation of the sleeve cavity to a specific pressure. Upon completion of the procedure, the device is removed from the patient.

Figure 45:
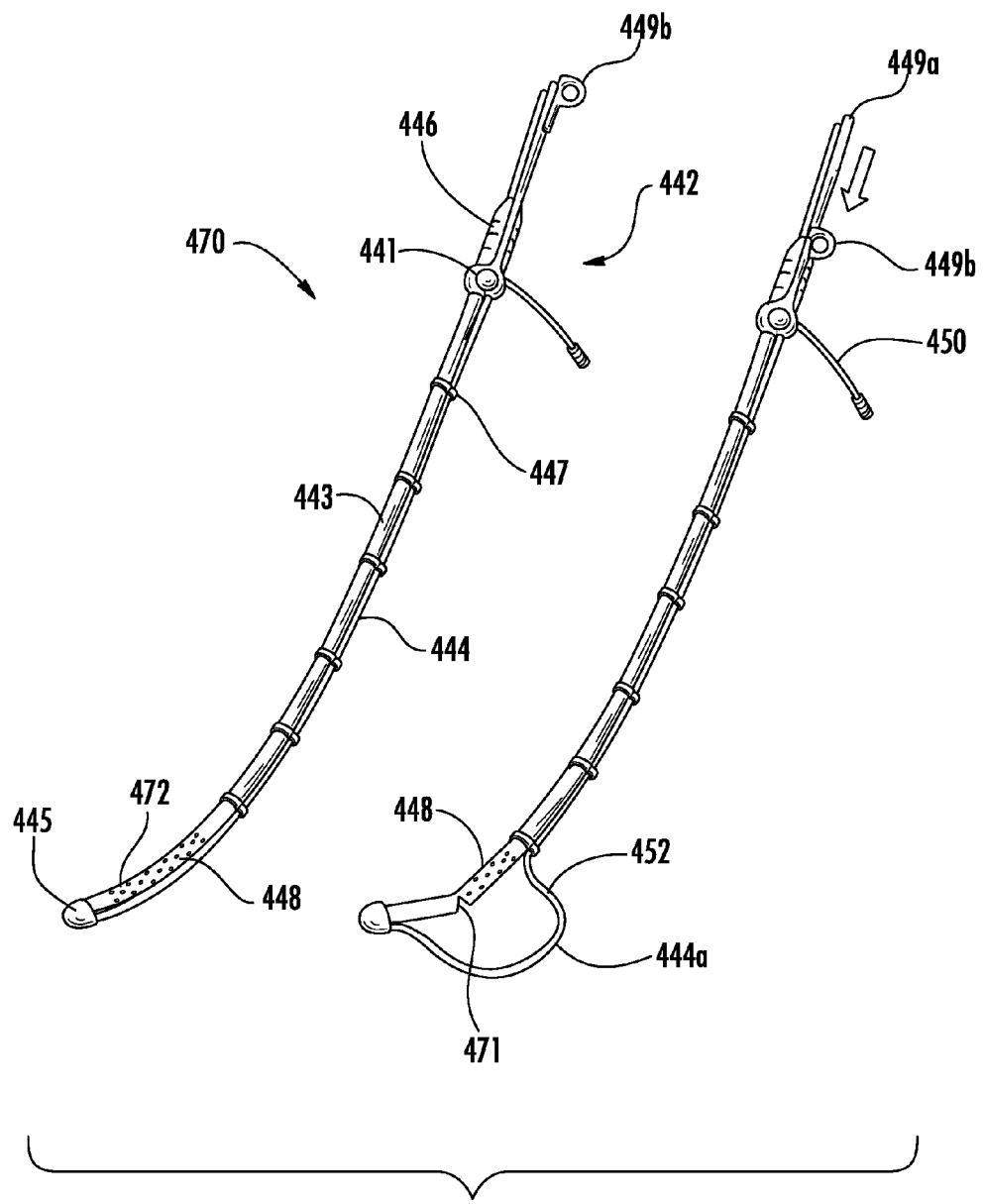

Turning now to FIG. 45, one embodiment of a gastrectomy device is shown generally identified by reference numeral 470 which similar to devices 440 and 460 but includes a pivot stress relief feature 471 located at a specific distance from the distal end of the main shaft 443 and an actuation wire 472 that travels to and through a lumen in the handle attached to the atraumatic tip 445 and within the ID of the main shaft 443.

In use, the main shaft 443 of the device is introduced into the patient through the mouth, down the esophagus, cannulating the esophageal sphincter, and placed distally at the area of the antrum and pylorus. The user then orients the device rotationally via the proximal handle such that the main shaft 443 is oriented against the inner curve of the stomach and the deflection shaft 444 is oriented toward the greater curve of the stomach. The actuation member 449*b* on the handle assembly 442 is then advanced distally, resulting in the bowing effect of the deflection shaft 444 to the degree that the arc of the shaft interfaces with the greater curve, putting the anterior and posterior sides of the stomach in tension and uniform about the distal geometry of the device. The actuation wire 472 is put in tension by the user, which deflects the distal end of the main shaft 443, pivoting about the pivot feature 471 and seating the distal end of the device in the antrum. Additionally, this deflection results in a resultant force causing the atraumatic distal end of the main shaft 443 to conform to the angularis and antrum. Suction is then applied through the main shaft 443, pulling the inner surfaces of the lesser curve against the perforated distal length of the main shaft 443 and deflating the stomach. This vacuum results in making the remodeled stomach static, to which the handle actuation member 449*b* can be returned to its fully proximal position, retracting the arc 444*a* of the deflection member 444 and returning it tangent to the main shaft 443. As tension is still applied to the actuation wire 472, the deflection of the main shaft 443 remains seated at the antrum and serves as an indicator to start resection. This is a visual guide for application of the staple line over the resected stomach. Once the resection is completed, the device allows for pressure testing of the newly remodeled sleeve by ceasing suction and allowing for insufflation of the sleeve cavity to a specific pressure. Upon completion of the procedure, tension of the actuation wire 472 is released and the device is removed from the patient.

It will be understood that various modifications may be made to the embodiments of the present disclosure herein.

Therefore, the above description should not be construed as limiting, but merely as exemplifications of embodiments. Those skilled in the art will envision other modifications within the scope and spirit of the present disclosure.

The invention claimed is:

1. A gastrectomy device, comprising:
   a tubular elongated member defining a centerline that extends through proximal and distal ends thereof, the elongated member defining a side opening; and
   a shape modification member being movable through the side opening of the elongated member and relative to the centerline of the elongated member between a first state, adjacent to the elongated member, and a second state, spaced from the elongated member, the shape modification member configured to conform to a portion of a patient's stomach in the second state, the shape modification member including a plurality of lights disposed along a longitudinal length thereof, the plurality of lights housed within the shape modification member.

2. The gastrectomy device of claim 1, further including an expandable member coupled to the distal end of the elongated member.

3. The gastrectomy device of claim 2, wherein the expandable member is a balloon.

4. The gastrectomy device of claim 1, wherein the elongated member is formed of a flexible material.

5. The gastrectomy device of claim 1, wherein the elongated member defines a lumen that extends longitudinally therethrough, the elongated member defining at least one aperture in the distal end thereof that is in fluid communication with the lumen, the lumen configured to couple to a vacuum source.

6. The gastrectomy device of claim 5, wherein at least a portion of the shape modification member is movable through the lumen and the side opening in response to linear movement of the shape modification member.

7. The gastrectomy device of claim 1, wherein the shape modification member forms an arc in the second state.

8. The gastrectomy device of claim 1, wherein the shape modification member is coupled to an actuator at a proximal end of the shape modification member, the actuator being movable to reposition the shape modification member between the first and second states.

9. The gastrectomy device of claim 1, wherein the elongated member includes a stress relief feature disposed at a predetermined distance from the distal end of the elongated member, the stress relief feature separating distal and proximal portions of the elongated member at a pivot point, the distal portion of the elongated member being pivotable relative to the proximal portion of the elongated member.

10. The gastrectomy device of claim 1, wherein the shape modification member is formed of a flexible material.

11. The gastrectomy device of claim 10, wherein in the second state, the shape modification member has a first looped portion and a second looped portion.

12. The gastrectomy device of claim 1, wherein the shape modification member is configured to form at least one loop in the second state.

13. The gastrectomy device of claim 1, wherein at least a portion of the shape modification member is magnetic.

14. The gastrectomy device of claim 1, wherein the shape modification member includes:
    a proximal portion;
    a free distal portion; and
    a pivot portion pivotably coupling the free distal portion to the proximal portion.

15. The gastrectomy device of claim 1, wherein the shape modification member includes a plurality of members movably coupled to one another and disposed proximally of a free distal portion of the shape modification member such that the shape modification member articulates between the first and second states.

16. The gastrectomy device of claim 1, wherein the shape modification member has a distal portion separable from the elongated member.

17. A gastrectomy device including:
    a tubular elongated member having an outer surface; and
    a shape modification member including a plurality of lights disposed along a longitudinal length thereof, the plurality of lights housed within the shape modification member, the shape modification member configured to emerge from an opening in the elongated member, the shape modification member including a proximal portion and a distal portion, the distal portion of the shape modification member being movable between a first state adjacent the outer surface of the elongated member and a second state spaced from the outer surface of elongated member, the distal portion configured to conform to a greater curvature portion of a patient's stomach in the second state.

18. The gastrectomy device of claim 17, further including at least one expandable member coupled to the elongated member, the at least one expandable member being expandable relative to a centerline of the elongated member between a contracted state and an expanded state to facilitate selective securement of a distal end of the elongated member within a patient's stomach.

19. The gastrectomy device of claim 17, wherein the elongated member defines a lumen that extends longitudinally therethrough, the elongated member defining at least one aperture in the distal end thereof that is in fluid communication with the lumen, the lumen configured to couple to a vacuum source.

* * * * *